(12) United States Patent
Bak-Boychuk et al.

(10) Patent No.: US 12,383,202 B2
(45) Date of Patent: Aug. 12, 2025

(54) DIRECT CARDIAC PRESSURE MONITORING

(71) Applicant: Edwards Lifesciences Corporation, Irvine, CA (US)

(72) Inventors: Gregory Bak-Boychuk, San Clemente, CA (US); Glen T. Rabito, Lake Forest, CA (US); Juan Valencia, Fullerton, CA (US); Joseph Arthur Passman, Costa Mesa, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 995 days.

(21) Appl. No.: 17/394,180

(22) Filed: Aug. 4, 2021

(65) Prior Publication Data

US 2021/0361238 A1    Nov. 25, 2021

Related U.S. Application Data

(63) Continuation of application No. PCT/US2020/015319, filed on Jan. 28, 2020.

(60) Provisional application No. 62/803,182, filed on Feb. 8, 2019.

(51) Int. Cl.
*A61B 5/0215* (2006.01)
*A61B 5/00* (2006.01)
*A61F 2/24* (2006.01)

(52) U.S. Cl.
CPC .......... *A61B 5/6869* (2013.01); *A61B 5/0215* (2013.01); *A61B 5/686* (2013.01); *A61B 5/6861* (2013.01); *A61B 5/6882* (2013.01); *A61F 2/246* (2013.01); *A61B 2560/066* (2013.01)

(58) Field of Classification Search
CPC ..... A61B 5/6869; A61B 5/0215; A61B 5/686; A61B 5/6861; A61B 5/6882; A61B 2560/066; A61B 17/0401; A61B 17/12031; A61B 17/12122; A61B 2017/00022; A61B 2017/00592; A61B 2017/00597; A61B 2017/00606; A61B 2017/00615; A61B 2017/00623; A61B 2017/00867; A61B 2017/0437; A61B 2017/0441; A61B 5/0031; A61B 5/076; A61B 17/0057; A61F 2/246; A61F 2/2409; A61F 2/2418; A61F 2/90
See application file for complete search history.

(56) References Cited

U.S. PATENT DOCUMENTS

| | | | |
|---|---|---|---|
| 6,855,115 B2 | 2/2005 | Fonseca et al. |
| 7,229,415 B2 | 6/2007 | Schwartz |
| 7,340,288 B1 | 3/2008 | Karicherla et al. |
| 7,509,169 B2 | 3/2009 | Eigler et al. |
| 7,931,597 B2 | 4/2011 | Bodecker et al. |
| 8,696,693 B2 | 4/2014 | Najafi et al. |
| 2002/0077556 A1 | 6/2002 | Schwartz |
| 2005/0065589 A1 | 3/2005 | Schneider et al. |
| 2006/0161171 A1 | 7/2006 | Schwartz |

(Continued)

FOREIGN PATENT DOCUMENTS

| | | |
|---|---|---|
| CN | 107530088 A | 1/2018 |
| WO | 2018213230 A1 | 11/2018 |

*Primary Examiner* — Andrey Shostak
(74) *Attorney, Agent, or Firm* — Chang and Hale LLP

(57) ABSTRACT

A septal closure device includes a frame comprising one or more tissue anchor features, an occluding membrane, and a pressure sensor device attached to the occluding membrane.

14 Claims, 30 Drawing Sheets

(56) References Cited

U.S. PATENT DOCUMENTS

| | | | |
|---|---|---|---|
| 2006/0224183 A1* | 10/2006 | Freudenthal | A61B 17/12031 606/213 |
| 2007/0049980 A1 | 3/2007 | Zielinski et al. | |
| 2007/0073351 A1 | 3/2007 | Zielinski et al. | |
| 2008/0051863 A1 | 2/2008 | Schneider et al. | |
| 2012/0022507 A1* | 1/2012 | Najafi | A61B 5/6869 606/1 |
| 2013/0165967 A1* | 6/2013 | Amin | A61B 17/0057 606/213 |
| 2014/0213916 A1 | 7/2014 | Doan et al. | |
| 2014/0275865 A1 | 9/2014 | Tammam et al. | |
| 2015/0112383 A1* | 4/2015 | Sherman | A61B 17/0057 606/213 |
| 2015/0157268 A1 | 6/2015 | Winshtein et al. | |
| 2016/0256141 A1* | 9/2016 | Mendez | A61B 17/0057 |
| 2018/0098772 A1 | 4/2018 | Goldshtein et al. | |

\* cited by examiner

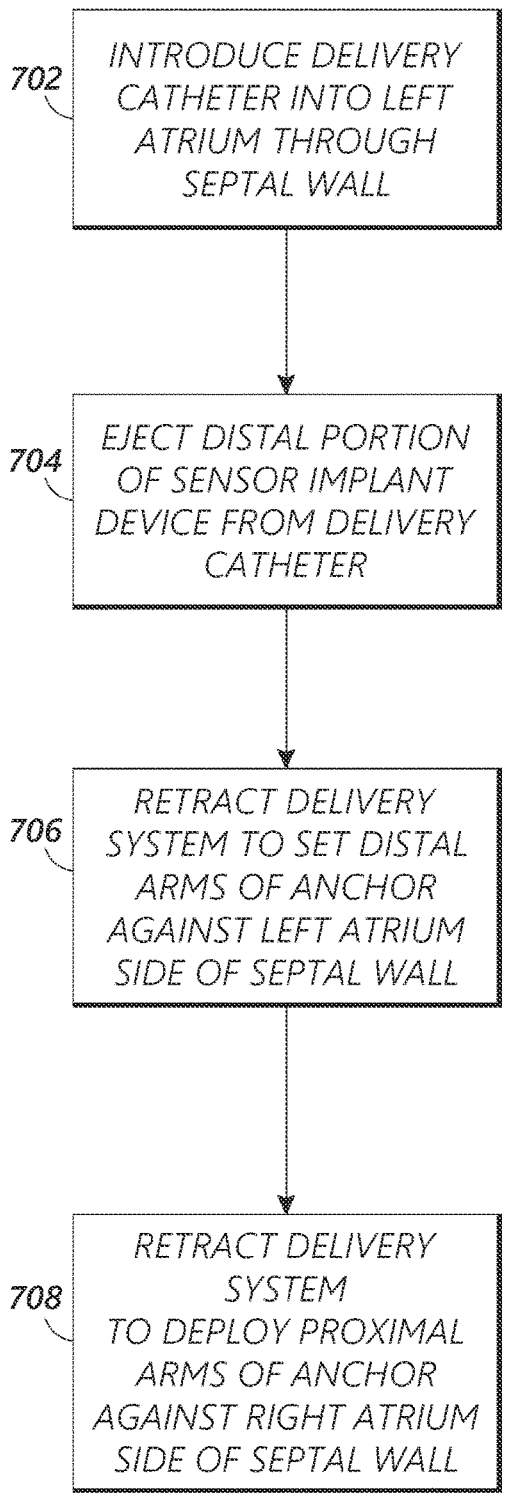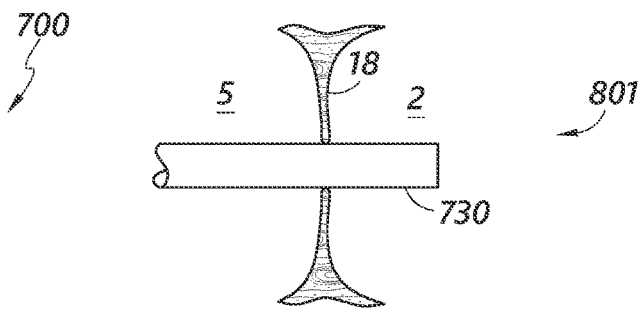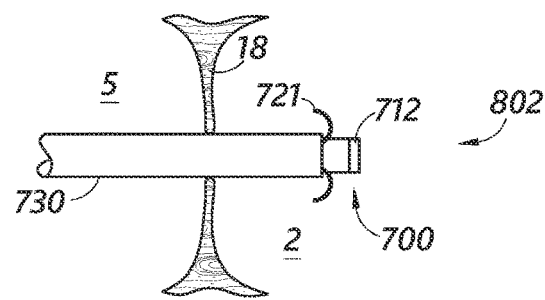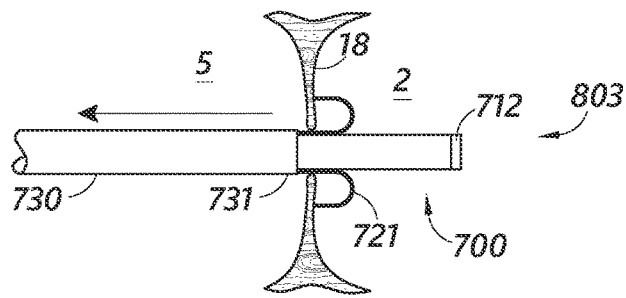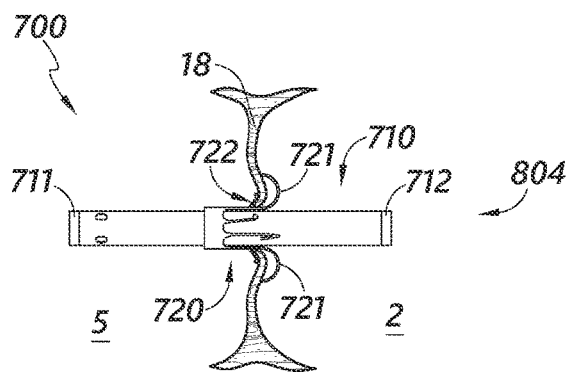
FIG. 7   FIG. 8

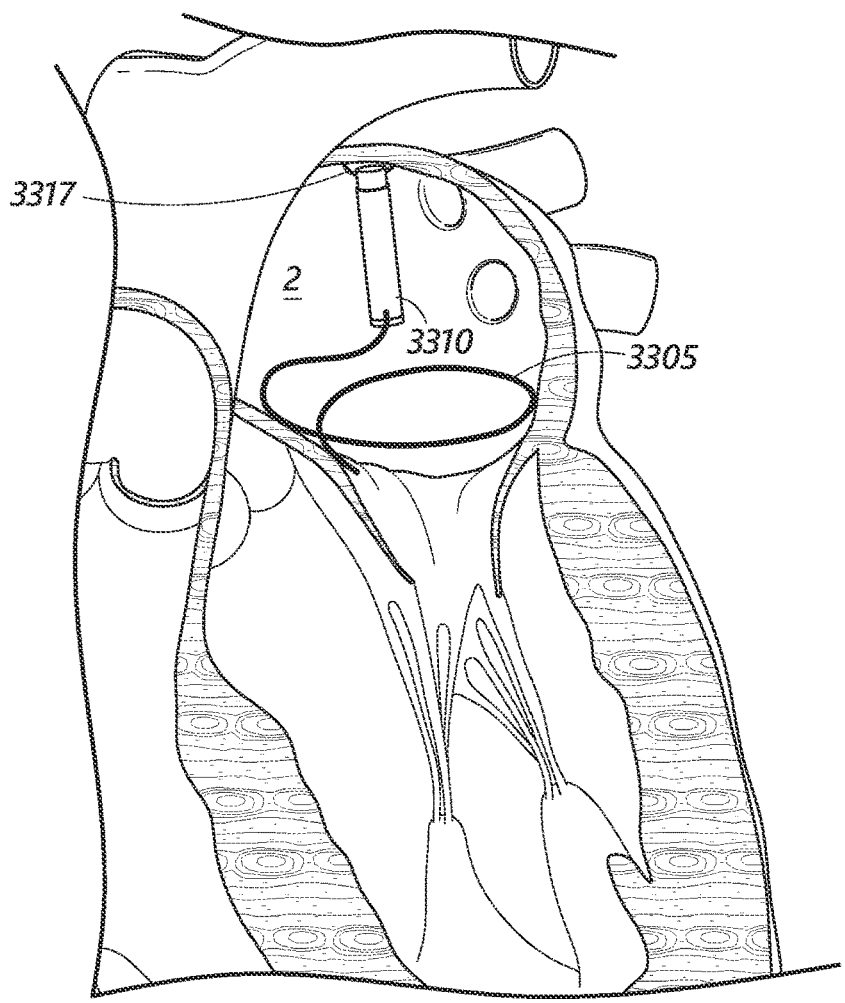
FIG. 33
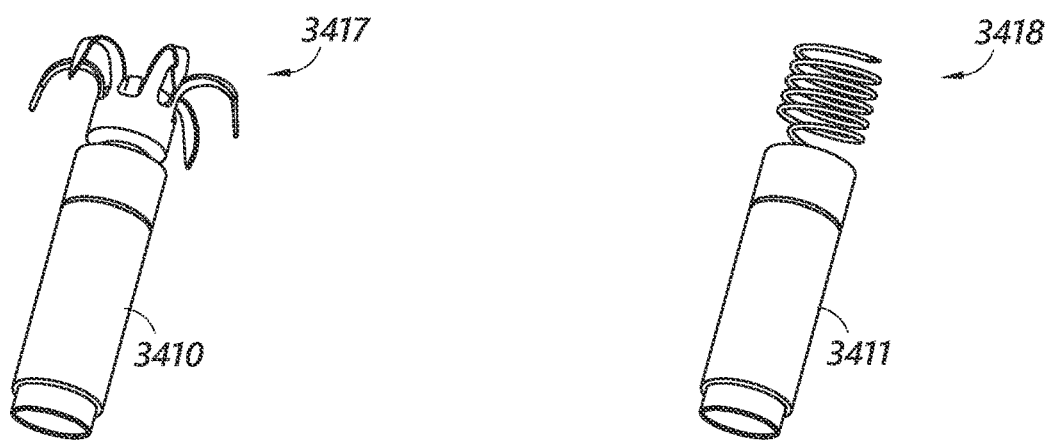
FIG. 34A
FIG. 34B

DIRECT CARDIAC PRESSURE MONITORING

RELATED APPLICATIONS

This application is a continuation application of International Patent Application Serial No. PCT/US2020/015319, filed Jan. 28, 2020, which claims priority to U.S. Provisional Application No. 62/803,182, filed on Feb. 8, 2019, both entitled DIRECT CARDIAC PRESSURE MONITORING, the disclosures of which are hereby incorporated by reference in their entireties.

BACKGROUND

Field

The present disclosure generally relates to the field of medical implant devices.

Description of Related Art

Various medical procedures involve the implantation of medical implant devices within the anatomy of the heart. Certain physiological parameters associated with such anatomy, such as fluid pressure, can have an impact on patient health.

SUMMARY

Described herein are one or more methods and/or devices to facilitate pressure sensing in cardiac anatomy. In some implementations, the present disclosure relates to a septal closure device comprising a frame comprising one or more tissue anchor features, an occluding membrane, and a pressure sensor device attached to the occluding membrane.

In some embodiments, the pressure sensor device comprises a first portion disposed on a first side of the occluding membrane and a second portion disposed on a second side of the occluding membrane. For example, the first portion of the pressure sensor device comprises a first pressure sensor element and the second portion of the pressure sensor device comprises a second pressure sensor element.

The occluding membrane may comprise a cloth. The occluding membrane may comprise a bio-spun polymer. The pressure sensor device may comprise a rigid cylindrical body. For example, the body of the pressure sensor device may have one or more radial projection features associated therewith. In some embodiments, the occluding membrane comprises a cuff feature configured to hold the sensor device. For example, the septal closure device may further comprise a suture collar wrapped at least partially around the cuff feature of the occluding membrane.

In some implementations, the present disclosure relates to an implant device comprising a leaflet spacer form, a first tether attached to a first end of the leaflet spacer form, a tissue anchor attached to the first tether, and a first pressure sensor device coupled to the leaflet spacer form. In some embodiments, the leaflet spacer form has a foam filler disposed therein. In some embodiments, the leaflet spacer form has an exterior recess and the first pressure sensor device is disposed at least partially within the recess. In some embodiments, the first pressure sensor device is disposed at least partially within the leaflet spacer form.

The implant device may further comprise a second tether attached to a second end of the leaflet spacer form, a second pressure sensor device attached to the second tether, and an anchor attached to the second sensor device. The anchor is configured to secure the second sensor device at least partially within a blood vessel. The blood vessel may be the inferior vena cava, wherein the second tether is configured to couple the second pressure sensor device to the leaflet spacer form through the right atrium.

In some implementations, the present disclosure relates to an edge-to-edge valve leaflet repair device comprising a first clasp member, a second clasp member, a spacer disposed between the first and second clasp members, the spacer having a ventricular base portion that is coupled to the first and second clasp members and an atrial end portion, and a pressure sensor device integrated with the spacer. In some embodiments, the pressure sensor device comprises a pressure sensor element that protrudes from the end portion of the spacer. In some embodiments, the valve leaflet repair device further comprises a second pressure sensor element associated with the base portion of the spacer.

In some implementations, the present disclosure relates to an implant device comprising a cylindrical elongate sensor device having a proximal end portion and a distal end portion, and a tissue anchor coupled to the sensor device, the tissue anchor comprising a plurality of curved distal arms, the plurality of distal arms being concave in a proximal direction with respect to the sensor device and having respective tissue-contact ends that point in the proximal direction in a deployment configuration and a plurality of at least partially straight proximal arms, the plurality of proximal arms being deflected away from the sensor device and projecting in a distal direction with respect to the sensor device.

The implant device may further comprise one or more projection features associated with the sensor device. For example, the sensor device may comprise a glass cylinder body and the one or more projection features may be attached to the cylinder body by an adhesive. In some embodiments, the sensor device comprises a first sensor element associated with the distal end portion and a second sensor element associated with the proximal end portion.

In some implementations, the present disclosure relates to an anchor comprising first and second coil portions having a first diameter and an intermediate coil portion disposed between the first and second coil portions and having a second diameter that is less than the first diameter. In some embodiments, the anchor comprises memory metal and the first and second coil portions are configured to be disposed in a delivery catheter in a compressed state and form a plurality of coils of the first diameter when deployed from the delivery catheter. The anchor may further comprise a cylinder form coupled to one or more coils of the intermediate coil portion by one or more projection features associated with the cylinder form. For example, the cylinder form may be a pressure sensor device.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

FIG. 7 is a flow diagram illustrating a process for implanting a sensor implant device in accordance with one or more embodiments of the present disclosure.

FIG. 8 illustrates states of components of a sensor implant device and/or an associated delivery system corresponding to the various steps of the process of FIG. 7 in accordance with one or more embodiments.

FIG. 33 illustrates a sensor device suspended in the left atrium using an anchor system in accordance with one or more embodiments.

FIGS. 34A and 34B illustrate example embodiments of pressure sensors having associated or integrated tissue anchors in accordance with one or more embodiments.

DETAILED DESCRIPTION

Figure 1:
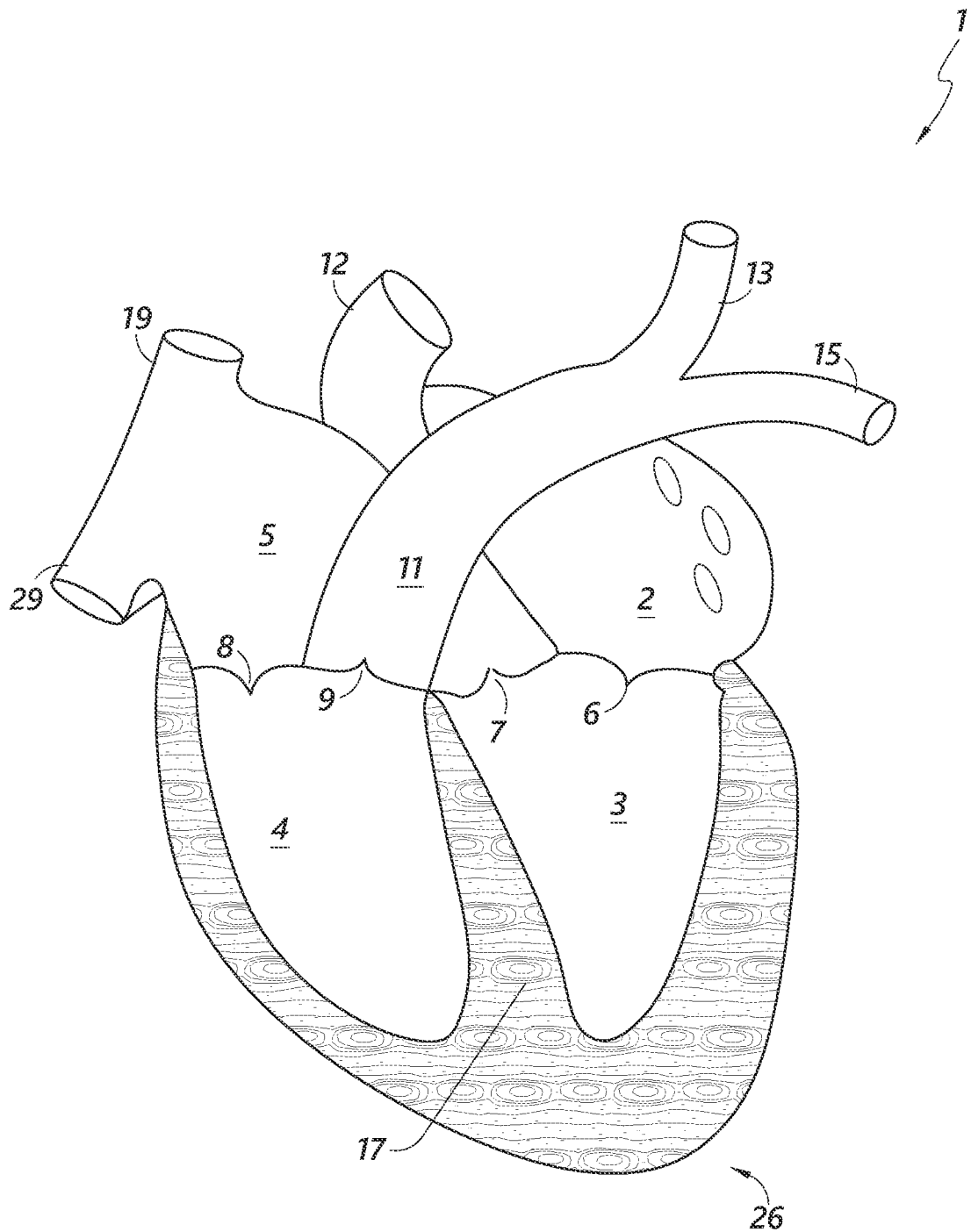
FIG. 1 is a cross-sectional view of a human heart.

The headings provided herein are for convenience only and do not necessarily affect the scope or meaning of the claimed invention.

The present disclosure relates to systems, devices, and methods for telemetric pressure monitoring in connection with cardiac implants and/or other medical implant devices and/or procedures. Such pressure monitoring may be performed using cardiac implant devices having integrated pressure sensors and/or associated components.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Embodiments of the present disclosure relate to cardiac pressure monitoring solutions including implant devices integrated with sensor functionality, such as pressure sensor functionality. For example, pressure monitoring solutions in accordance with embodiments of the present disclosure may be applicable for patients suffering from various forms of heart failure, such as acute congestive heart failure. Pressure monitoring solutions as disclosed herein may allow for improved diagnostics and/or notification relating to heart conditions. For example, embodiments of the present disclosure allow for cardiac pressure monitoring of a patient post-operatively, wherein the pressure monitoring may involve tracking and/or notification of pressure trends (or trends relating to one or more other physiological parameters monitored in accordance with the present disclosure) that may result in or be associated with adverse effects or events. The various embodiments disclosed herein involve sensor-integrated implant devices implanted in various vessels or chambers of the cardiac system. Furthermore, various embodiments disclosed herein relate to sensor-integrated implants of various types, including septal closure or occluder devices, leaflet repair spacers, leaflet clip devices, and the like.

Certain embodiments are disclosed herein in the context of cardiac implant devices. However, although certain principles disclosed herein are particularly applicable to the anatomy of the heart, it should be understood that sensor implant devices in accordance with the present disclosure may be implanted in, or configured for implantation in, any suitable or desirable anatomy.

The anatomy of the heart is described below to assist in the understanding of certain inventive concepts disclosed herein. In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.). The contraction of the various heart muscles may be prompted by signals generated by the electrical system of the heart, which is discussed in detail below. Certain embodiments disclosed herein relate to conditions of the heart, such as atrial fibrillation and/or complications or solutions associated therewith. However, embodiments of the present disclosure relate more generally to any health complications relating to fluid overload in a patient, such as may result post-operatively after any surgery involving fluid supplementation. That is, detection of atrial stretching as described herein may be implemented to detect/determine a fluid-overload condition, which may direct treatment or compensatory action relating to atrial fibrillation and/or any other condition caused at least in part by fluid overloading.

FIG. 1 illustrates an example representation of a heart 1 having various features relevant to certain embodiments of the present inventive disclosure. The heart 1 includes four chambers, namely the left atrium 2, the left ventricle 3, the right ventricle 4, and the right atrium 5. In terms of blood flow, blood generally flows from the right ventricle 4 into the pulmonary artery via the pulmonary valve 9, which separates the right ventricle 4 from the pulmonary artery 11 and is configured to open during systole so that blood may be pumped toward the lungs and close during diastole to prevent blood from leaking back into the heart from the pulmonary artery 11. The pulmonary artery 11 carries deoxygenated blood from the right side of the heart to the lungs. The pulmonary artery 11 includes a pulmonary trunk and left 15 and right 13 pulmonary arteries that branch off of the pulmonary trunk, as shown. In addition to the pulmonary valve 9, the heart 1 includes three additional valves for aiding the circulation of blood therein, including the tricuspid valve 8, the aortic valve 7, and the mitral valve 6. The tricuspid valve 8 separates the right atrium 5 from the right ventricle 4. The tricuspid valve 8 generally has three cusps or leaflets and may generally close during ventricular contraction (i.e., systole) and open during ventricular expansion (i.e., diastole). The mitral valve 6 generally has two cusps/leaflets and separates the left atrium 2 from the left ventricle 3. The mitral valve 6 is configured to open during diastole so that blood in the left atrium 2 can flow into the left ventricle 3, and, when functioning properly, closes during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage. Disfunction of a heart valve and/or associated leaflets (e.g., pulmonary valve disfunction) can result in valve leakage and/or other health complications.

The atrioventricular (i.e., mitral and tricuspid) heart valves may further comprise a collection of chordae tendineae and papillary muscles (not shown) for securing the leaflets of the respective valves to promote and/or facilitate proper coaptation of the valve leaflets and prevent prolapse thereof. The papillary muscles, for example, may generally comprise finger-like projections from the ventricle wall. The valve leaflets are connected to the papillary muscles by the chordae tendineae. A wall of muscle 17, referred to as the septum, separates the left 2 and right 5 atria and the left 3 and right 4 ventricles.

As referenced above, certain physiological conditions or parameters associated with the cardiac anatomy can impact the health of a patient. For example, congestive heart failure is a condition associated with the relatively slow movement of blood through the heart and/or body, which can cause the fluid pressure in one or more chambers of the heart to increase. As a result, the heart does not pump sufficient oxygenated blood to meet the body's needs. The various chambers of the heart may respond to pressure increases by stretching to hold more blood to pump through the body or by becoming relatively stiff and/or thickened. The walls of the heart can eventually weaken and become unable to pump as efficiently. In some cases, the kidneys may respond to cardiac inefficiency by causing the body to retain fluid. Fluid build-up in arms, legs, ankles, feet, lungs, and/or other organs can cause the body to become congested, which is referred to as congestive heart failure. Acute decompensated congestive heart failure is a leading cause of morbidity and mortality, and therefore treatment and/or prevention of congestive heart failure is a significant concern in medical care.

The treatment and/or prevention of heart failure (e.g., congestive heart failure) can advantageously involve the monitoring of pressure in one or more chambers or regions of the heart or other anatomy. As described above, pressure buildup in one or more chambers or areas of the heart can be associated with congestive heart failure. Without direct or indirect monitoring of cardiac pressure, it can be difficult to infer, determine, or predict the presence or occurrence of congestive heart failure. For example, treatments or approaches not involving direct or indirect pressure monitoring may involve measuring or observing other present physiological conditions of the patient, such as measuring body weight, thoracic impedance, right heart catheterization, or the like.

Various methods for identifying and/or treating congestive heart failure involve the observation of worsening congestive heart failure symptoms and/or changes in body weight. However, such signs may appear relatively late and/or be relatively unreliable. For example, daily body-weight measurements may vary significantly (e.g., up to 9% or more) and may be unreliable in signaling heart-related complications. Furthermore, treatments guided by monitoring signs, symptoms, weight, and/or other biomarkers have not been shown to substantially improve clinical outcomes. In addition, for patients that have been discharged, such treatments may necessitate remote telemedicine systems. In some situations, congestive heart failure can result from fluid build-up over a period of time, such as a 2-3-week period. Therefore, detection and/or determination of fluid build-up within the initial days or week of fluid build-up can be useful in preventing development of congestive heart failure from fluid-build up over an extended period of time.

The present disclosure provides systems, devices, and methods for guiding the administration of medication relating to the treatment of congestive heart failure at least in part by directly monitoring pressure in the left atrium, or other chamber or vessel for which pressure measurements are indicative of left atrial pressure, in order to reduce hospital readmissions, morbidity, and/or otherwise improve the health prospects of patients.

Cardiac Pressure Monitoring

Cardiac pressure monitoring in accordance with embodiments the present disclosure may provide a proactive intervention mechanism for preventing or treating congestive heart failure. Generally, increases in ventricular filling pressures associated with diastolic and/or systolic heart failure can occur prior to the occurrence of symptoms that lead to hospitalization. For example, cardiac pressure indicators may present weeks prior to hospitalization with respect to some patients. Therefore, pressure monitoring systems in accordance with embodiments the present disclosure may advantageously be implemented to reduce instances of hospitalization by guiding the appropriate or desired titration and/or administration of medications before the onset of heart failure.

Figure 2:
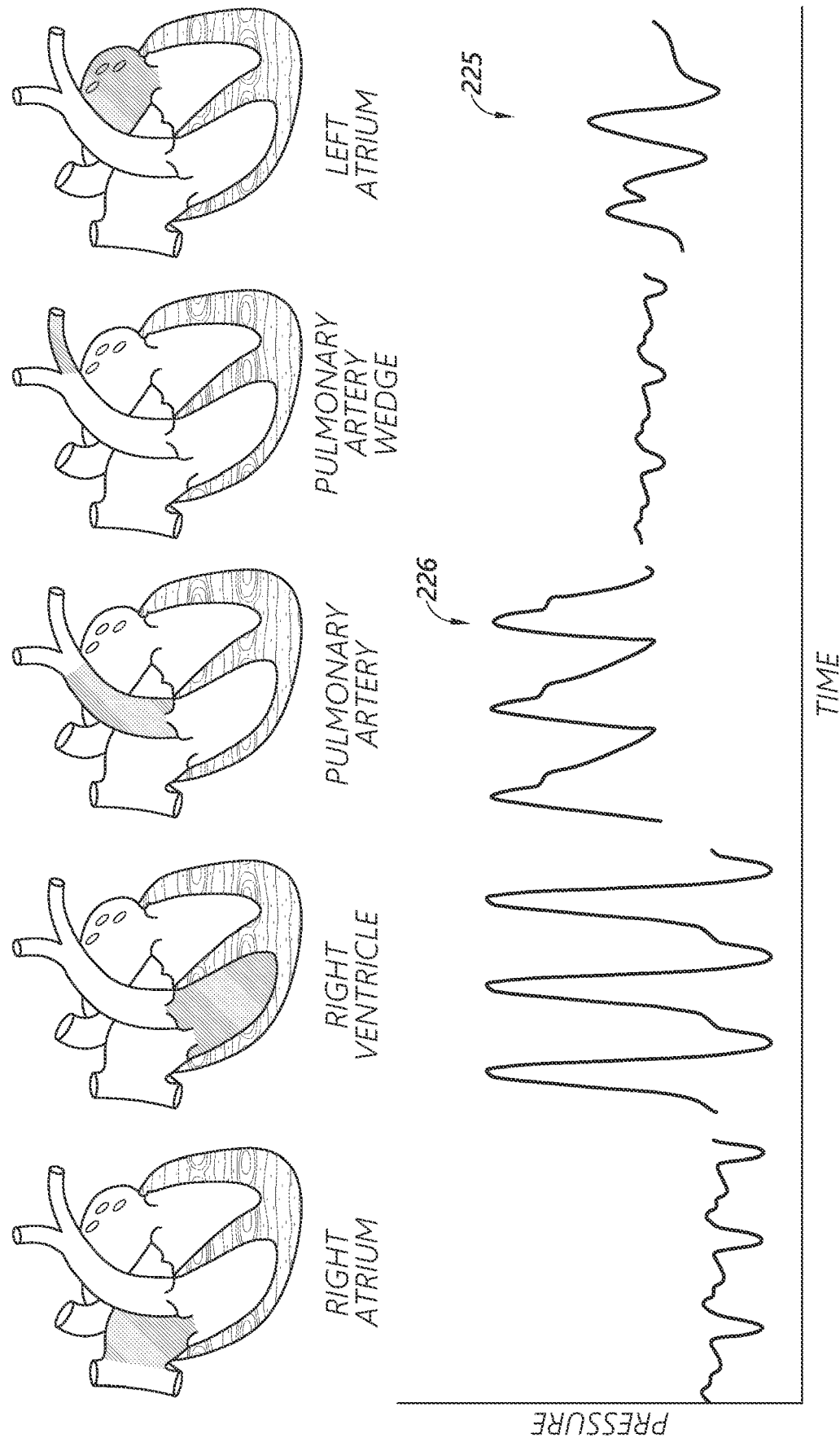
FIG. 2 illustrates example pressure waveforms associated with various chambers and vessels of the heart according to one or more embodiments.

As referenced above, with respect to cardiac pressures, pressure elevation in the left atrium may be particularly correlated with heart failure. FIG. 2 illustrates example pressure waveforms associated with various chambers and vessels of the heart according to one or more embodiments. The various waveforms illustrated in FIG. 2 may represent waveforms obtained using right heart catheterization to advance one or more pressure sensors to the respective illustrated and labeled chambers or vessels of the heart. As illustrated in FIG. 2, the waveform 225, which represents left atrial pressure, may be considered to provide the best feedback for early detection of congestive heart failure. Furthermore, there may generally be a relatively strong correlation between increases and left atrial pressure and pulmonary congestion.

Cardiac pressure monitoring, such as left atrial pressure monitoring, can provide a mechanism to guide administration of medication to treat and/or prevent congestive heart failure. Such treatments may advantageously reduce hospital readmissions and morbidity, as well as provide other benefits. An implanted pressure sensor in accordance with embodiments the present disclosure may be used to predict heart failure up two weeks or more before the manifestation of symptoms or markers of heart failure (e.g., dyspnea). When heart failure predictors are recognized using cardiac pressure sensor embodiments in accordance with the present disclosure, certain prophylactic measures may be implemented, including medication intervention, such as modification to a patient's medication regimen, which may help prevent or reduce the effects of cardiac dysfunction. Direct pressure measurement in the left atrium can advantageously provide an accurate indicator of pressure buildup that may lead to heart failure or other complications. For example, trends of atrial pressure elevation may be analyzed or used to determine or predict the onset of cardiac dysfunction, wherein drug or other therapy may be augmented to cause reduction in pressure and prevent or reduce further complications.

The sensor-integrated implant devices of the present disclosure may be implemented in various locations of the human anatomy. For example, a variety of cardiac anatomy locations may be used for sensor-integrated implant device implantation for the purpose of hemodynamic pressure measurement within the cardiovascular system. The implant devices disclosed herein may include one or more sensors integrated with an implant structure that serves one or more additional purposes in addition to pressure monitoring, such as shunting, tissue closure/occluding, repairing, or otherwise treating certain heart anatomy and/or conditions. Implant devices in accordance with the present disclosure may be implanted in any cardiac vessel or chamber, including the superior vena cava, inferior vena cava, right atrium, left atrium, right ventricle, left ventricle, pulmonary artery, pulmonary vein, coronary sinus, and/or the like.

Sensor-Integrated Implant Devices

Embodiments of the present disclosure may provide a mechanism for guiding administration of medication to a patient by monitoring left atrial pressure and/or other physiological conditions of the patient sensed by one or more sensor-integrated implant devices. With respect to congestive heart failure patients, such monitoring may help to reduce hospital readmissions and/or morbidity. In some implementations, a sensor-integrated implant device may be configured to detect physiological parameters or conditions indicative or predictive of heart failure or other condition(s) one or more weeks prior to manifestation of symptoms related therewith, such as dyspnea. Therefore, embodiments the present disclosure may advantageously facilitate modification of drug regimens or other treatments relatively early, potentially preventing more serious conditions or symptoms from developing. For example, early detection of pressure elevation in the left atrium may be used to determine trends in pressure elevation, wherein drug therapy may be augmented to drop left atrial pressure when detected or predicted to prevent further complications. With respect to heart failure related to fluid build-up in the lungs, such fluid build-up may typically gradually develop over one or more weeks, and therefore preliminary detection of increased pressure that may lead to such fluid build-up may allow for relatively early intervention and/or prevention.

Figure 3:
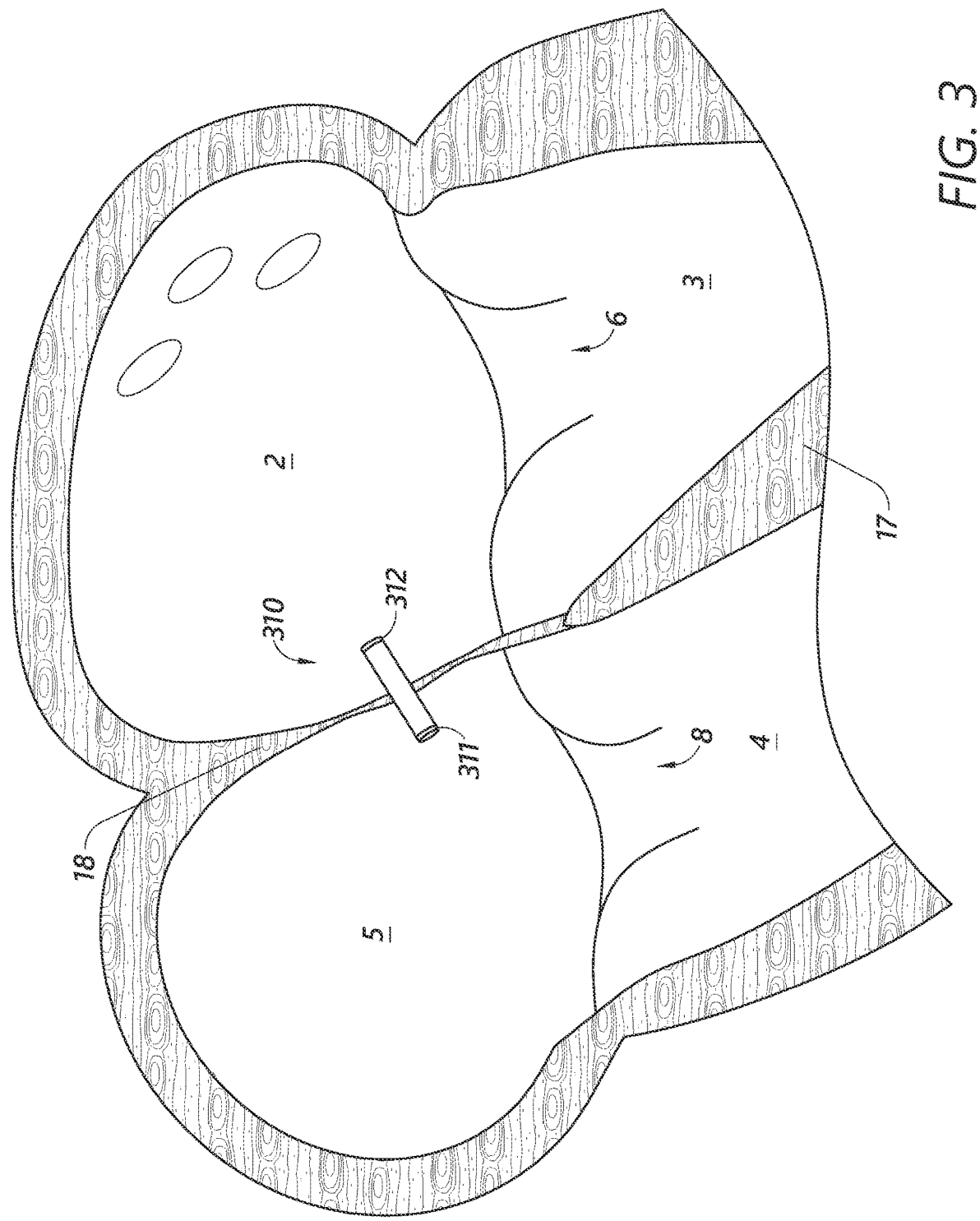
FIG. 3 illustrates an implanted sensor implant device in accordance with one or more embodiments.

FIG. 3 shows a sensor implant device 310 implanted in an atrial septum 18 in accordance with one or more embodiments. The particular position in the interatrial septum wall may be selected or determined in order to provide a relatively secure anchor location for the implant 310, as well as to provide a relatively low risk of thrombus. Furthermore, the sensor implant device 310 may be implanted at a position that is desirable in consideration of future re-crossing of the septal wall 18 for future interventions. Implantation of the sensor implant device 310 in the interatrial septum wall 18 may advantageously allow for communication between the left 2 and right 5 atria. With the device 310 in the atrial septum 18, the sensor element(s) 311, 312 of the sensor implant device 310 may advantageously be configured to measure pressure in the right atrium 5, the left atrium 2, or both atria. Although two sensor elements 311, 312 are shown, in some embodiments, the sensor implant 310 comprise a single sensor element, or more than two sensor elements. With pressure sensor functionality for measuring pressure in both atria, the sensor implant device 310 may advantageously be configured to provide sensor signals that may be used to determine differential pressure between the atria. Differential pressure determination may be useful for monitoring fluid build-up in the lungs, which may be associated with congestive heart failure.

With the sensor 310 implanted or disposed in the atrial septum 18, as shown, pressure may be monitored in either or both the right atrium 5 and the left atrium 2. For sensor embodiments comprising pressure sensor transducers disposed in both atria, the implant device 310 may provide the ability to measure differential pressure between the atria, which may be useful when monitoring fluid build-up in the lungs, which is associated with congestive heart failure as described above.

Generally, the atrial septal wall 18 may provide a good anchoring location for a pressure sensor 310. The sensor device 310 may advantageously be anchored in a secure location in the atrial wall 18. Furthermore, it may be desirable for the sensor 310 to be configured and/or constructed such that it presents a relatively low risk of thrombus with respect to the portion of the sensor device 310 disposed in the left atrium 2. In some embodiments, the present disclosure provides sensor-integrated implant devices that may be implanted in the interatrial septal wall 18, such that the implant device provides a mechanism for access for re-crossing the septal wall 18 for future medical interventions.

Figure 4:
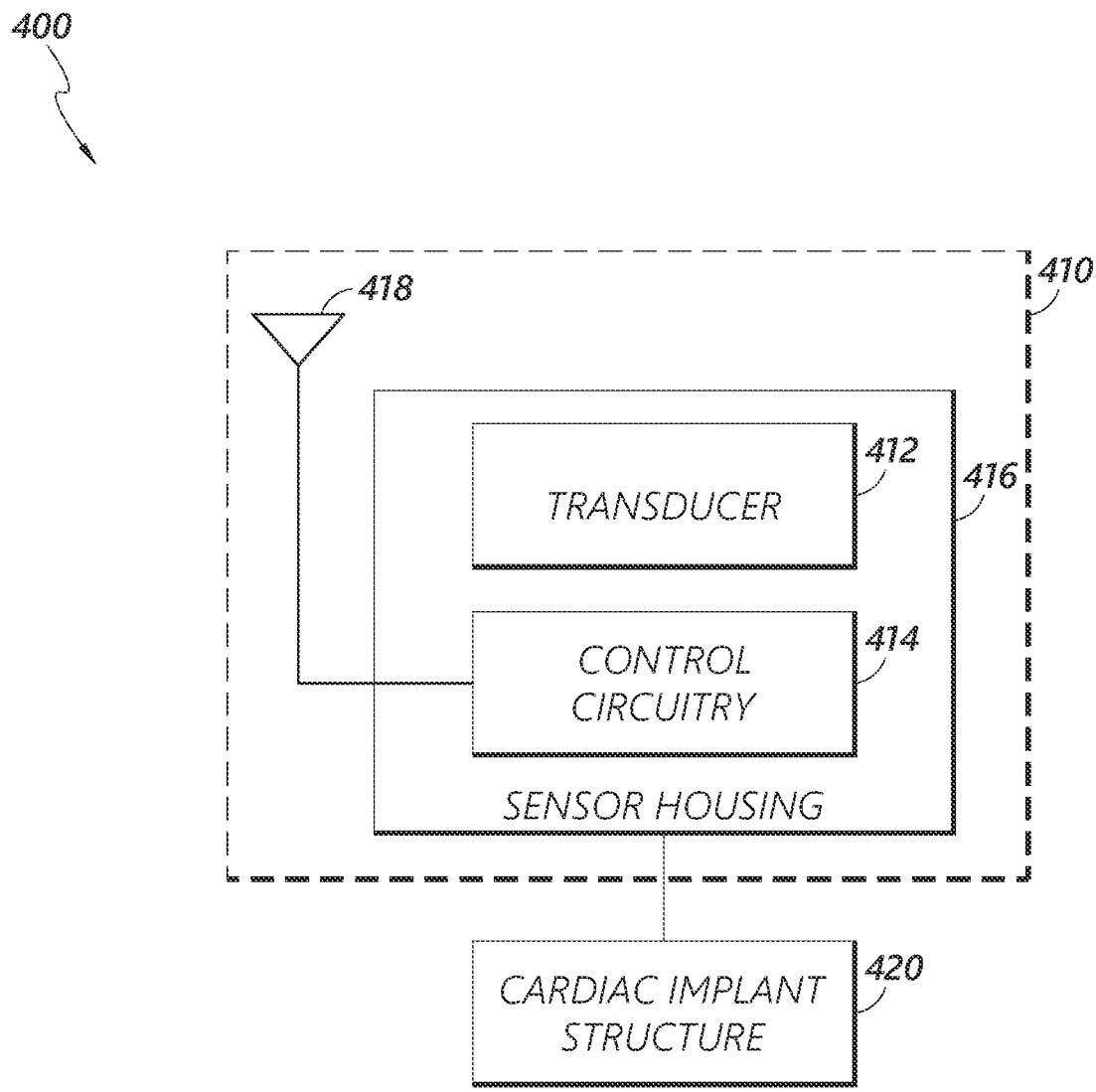
FIG. 4 is a block diagram of an implant device in accordance with one or more embodiments.

In some implementations, the present disclosure relates to pressure sensors associated or integrated with cardiac implant devices. Such sensor-integrated cardiac implant devices may be used to provide controlled and/or more effective therapies for treating and preventing heart failure. FIG. 4 is a block diagram illustrating an implant device 400 comprising a cardiac implant structure 420. In some embodiments, the cardiac implant structure 420 is physically integrated with and/or connected to a sensor device 410. The sensor device 410 may be, for example, a pressure sensor, or other type of sensor. In some embodiments, the sensor 410 comprises a transducer 412, such as a pressure transducer, as well as certain control circuitry 414, which may be embodied in, for example, an application-specific integrated circuit (ASIC). The control circuitry 414 may be configured to process signals received from the transducer 412 and/or communicate signals associated therewith wirelessly through biological tissue using the antenna 418. The antenna 418 may comprise one or more coils or loops of conductive material, such as copper wire or the like. In some embodiments, at least a portion of the transducer 412, control circuitry 414, and/or the antenna 418 are at least partially disposed or contained within a sensor housing 416, which may comprise any type of material, and may advantageously be at least partially hermetically sealed. For example, the housing 416 may comprise glass or other rigid material in some embodiments, which may provide mechanical stability and/or protection for the components housed therein. In some embodiments, the housing 416 is at least partially flexible. For example, the housing may comprise polymer or other flexible structure/material, which may advantageously allow for folding, bending, or collapsing of the sensor 410 to allow for transportation thereof through a catheter or other introducing means.

The transducer 412 may comprise any type of sensor means or mechanism. For example, the transducer 412 may be a force-collector-type pressure sensor. In some embodiments, the transducer 412 comprises a diaphragm, piston, bourdon tube, bellows, or other strain- or deflection-measuring component(s) to measure strain or deflection applied over an area/surface thereof. The transducer 412 may be associated with the housing 416, such that at least a portion thereof is contained within or attached to the housing 316. The term "associated with" is used herein according to its broad and ordinary meaning. With respect to sensor devices/components being "associated with" a stent or other implant structure, such terminology may refer to a sensor device or component being physically coupled, attached, or connected to, or integrated with, the implant structure.

In some embodiments, the transducer 412 comprises or is a component of a piezoresistive strain gauge, which may be configured to use a bonded or formed strain gauge to detect strain due to applied pressure, wherein resistance increases as pressure deforms the component/material. The transducer 412 may incorporate any type of material, including but not limited to silicon (e.g., monocrystalline), polysilicon thin film, bonded metal foil, thick film, silicon-on-sapphire, sputtered thin film, and/or the like.

In some embodiments, the transducer 412 comprises or is a component of a capacitive pressure sensor including a diaphragm and pressure cavity configured to form a variable capacitor to detect strain due to pressure applied to the diaphragm. The capacitance of the capacitive pressure sensor may generally decrease as pressure deforms the diaphragm. The diaphragm may comprise any material(s), including but not limited to metal, ceramic, silicon or other semiconductor, and the like. In some embodiments, the transducer 412 comprises or is a component of an electromagnetic pressure sensor, which may be configured to measure the displacement of a diaphragm by means of changes in inductance, linear variable displacement transducer (LVDT) functionality, Hall Effect, or eddy current sensing. In some embodiments, the transducer 412 comprises or is a component of a piezoelectric strain sensor. For example, such a sensor may determine strain (e.g., pressure) on a sensing mechanism based on the piezoelectric effect in certain materials, such as quartz. This technology is commonly employed for the measurement of highly dynamic pressures.

In some embodiments, the transducer 412 comprises or is a component of a strain gauge. For example, a strain gauge embodiment may comprise a pressure sensitive element on or associated with an exposed surface of the transducer 412. In some embodiments, a metal strain gauge is adhered to the sensor surface, or a thin-film gauge may be applied on the sensor by sputtering or other technique. The measuring element or mechanism may comprise a diaphragm or metal foil. The transducer 412 may comprise any other type of sensor or pressure sensor, such as optical, potentiometric, resonant, thermal, ionization, or other types of strain or pressure sensors.

In certain embodiments, the sensor 410 is configured to communicate with an external (e.g., non-implantable) device or system that includes an external reader (e.g., coil), which may include a wireless transceiver that is electrically and/or communicatively coupled to certain control circuitry. In certain embodiments, both the sensor 410 and the external subsystem include a corresponding coil antenna for wireless communication and/or power delivery through patient tissue disposed therebetween when the sensor 410 is implanted in a patient.

The external reader/monitor (not shown) can receive the wireless signal transmissions and/or provide wireless power using an external antenna, such as a wand device or other handheld reader or device. The external transceiver can include radio-frequency (RF) front-end circuitry configured to receive and amplify the signals from the sensor 410, wherein such circuitry can include one or more filters (e.g., band-pass filters), amplifiers (e.g., low-noise amplifiers), analog-to-digital converters (ADC) and/or digital control interface circuitry, phase-locked loop (PLL) circuitry, signal mixers, or the like. The external transceiver can further be configured to transmit signals over a network to a remote monitor subsystem or device. The RF circuitry of the external transceiver can further include one or more of digital-to-analog converter (DAC) circuitry, power amplifiers, low-pass filters, antenna switch modules, antennas or the like for treatment/processing of transmitted signals over a network and/or for receiving signals from the sensor 410. In certain embodiments, the external monitor includes control circuitry for performing processing of the signals received from the sensor 410. In certain embodiments, the external monitor is a smartphone, laptop computer, or other mobile computing device, or any other type of computing device.

In certain embodiments, the sensor 410 includes some amount of volatile and/or non-volatile data storage. For example, such data storage can comprise solid-state memory utilizing an array of floating-gate transistors, or the like. The control circuitry 414 may utilize data storage for storing sensed data collected over a period of time, wherein the stored data can be transmitted periodically to an external monitor or other external subsystem. In certain embodiments, the sensor 410 does not include any data storage. The control circuitry 414 is configured to facilitate wireless transmission of data generated by the sensor transducer(s) 412, or other data associated therewith. The control circuitry 414 may further be configured to receive input from one or more external subsystems, such as from an external reader (e.g., wand device), or from a remote monitor over, for example, a communications network (e.g., the Internet). For example, the sensor 410 may be configured to receive signals that at least partially control the operation of the sensor 410, such as by activating/deactivating one or more components or sensors, or otherwise affecting operation or performance of the sensor 410.

The one or more components of the sensor 410 can be powered by one or more power sources (not shown). Due to size, cost and/or electrical complexity concerns, it may be desirable for such power source(s) to be relatively minimalistic in nature. For example, high-power driving voltages and/or currents in the sensor 410 may adversely affect or interfere with operation of the heart or other body part associated with the implant device 400. In certain embodiments, the sensor 410 is configured to receive power from an external source wirelessly by passive circuitry of the sensor 410, such as through the use of short-range, or near-field wireless power transmission, or other electromagnetic coupling mechanism. For example, an external device may be used as an initiator that actively generates an RF field that can provide power to the sensor 410, thereby allowing the power circuitry of the implant device 400 to take a relatively simple form factor. In certain embodiments, the implant device 400 is configured to harvest energy from environmental sources, such as fluid flow, motion, or the like. Additionally or alternatively, the implant device 400 can comprise a battery, which can advantageously be configured to provide enough power as needed over the monitoring period (e.g., 1, 2, 3, 5, 10, 20, 30, 60, or 90 days, or other period of time).

In some embodiments, the sensor 410 is configured to operate with a local reader/monitor that comprises a wearable communication device, or other device that can be readily disposed in proximity to the patient and sensor 410. Such external reader/monitor device/system be configured to continuously, periodically, or sporadically interrogate the sensor 410 in order to extract or request sensor-based information therefrom. In certain embodiments, a user interface may be implemented that allows a user to utilize the interface to view sensor data, request sensor data, or otherwise interact with the sensor 410.

In certain embodiments, an external reader/monitor comprises a coil antenna that is matched and/or tuned to be inductively paired with the antenna 418 of the internal implant device 410. In some embodiments, the sensor 410 is configured to receive wireless ultrasound power charging and/or data communication between from an external monitor system.

Figure 5:
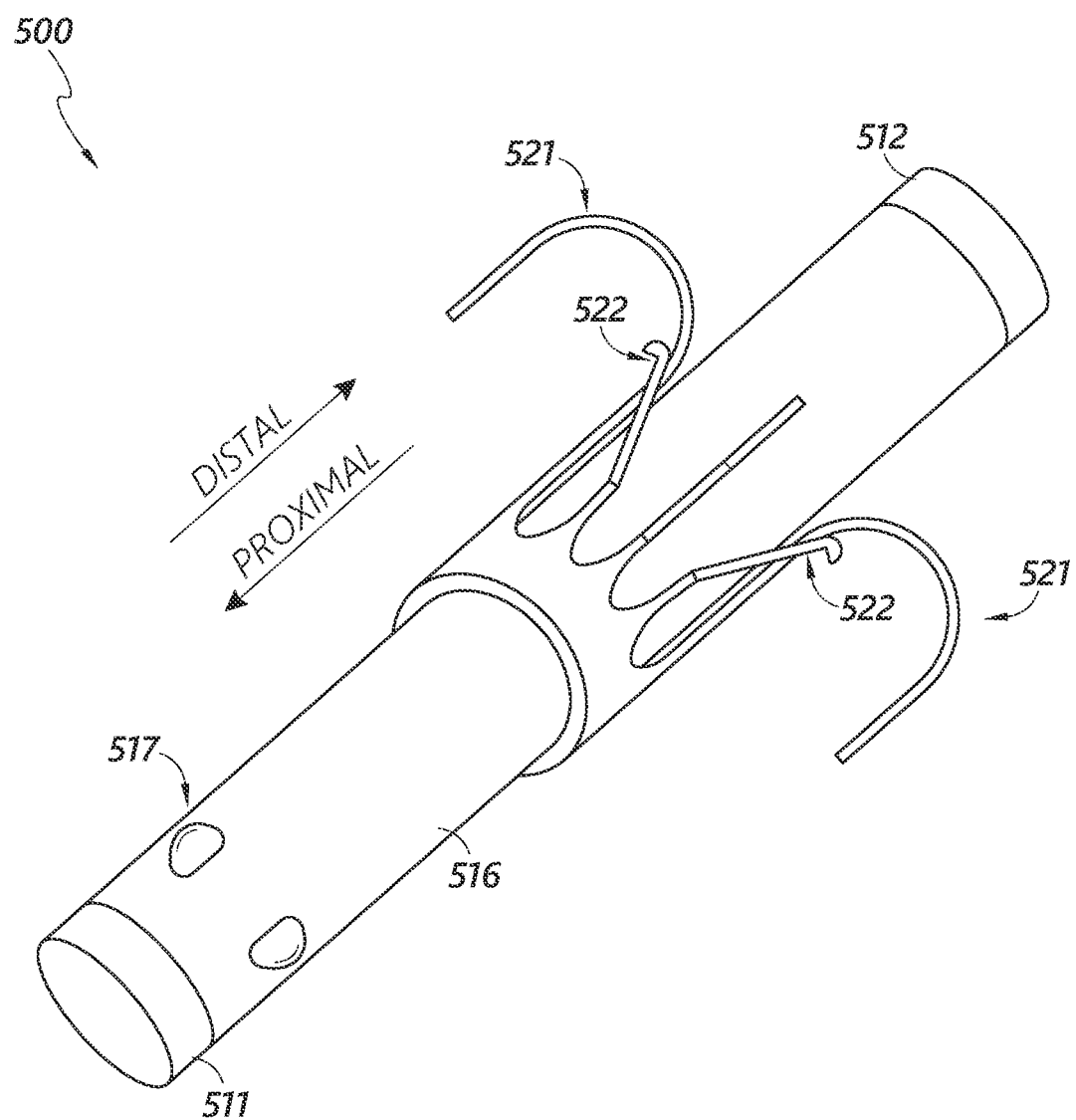
FIG. 5 illustrates a perspective view of a sensor implant device in accordance with one or more embodiments.

FIG. 5 illustrates a perspective view of a sensor implant device 500 in accordance with one or more embodiments. The sensor implant device 500 comprises a sensor 510, which may have a generally-cylindrical form with respect to one or more portions thereof. However, it should be understood that although certain embodiments are disclosed herein in the context of cylindrical sensor devices, the principles of the present disclosure relate to sensor implant devices comprising sensors having any suitable or desirable shape, form, or configuration.

The sensor device 510 may comprise one or more sensors 511, 512, such as pressure transducers, which may be associated with one or more distal or proximal end portions of the sensor 510. For example, the sensor 510 may comprise a first sensor element 512, which may be considered a distal sensor element, as well as a second sensor element 511, which may be considered a proximal sensor element in some embodiments. The sensor implant device 500 includes an anchor 520, which may comprise one or more arms 521, 522 for securing the sensor implant device 500 to a tissue wall, such as and atrial septal wall. The anchor 520 may comprise memory metal or other material and may be a fixed or attached in some manner to the sensor 510. The anchor arms 521, 522 of the anchor 520 may comprise one or more distal arms 521 and one or proximal arms 522, which are described in further detail below. In some embodiments, the sensor 510 includes or is associated with one or more projection features 517, which may comprise knobs, projections, extensions, teeth, grooves, posts, or the like, and may be used to secure the sensor 510 to one or more components of a delivery system (not shown) or to one or more features of the anchor 520.

Figure 6:
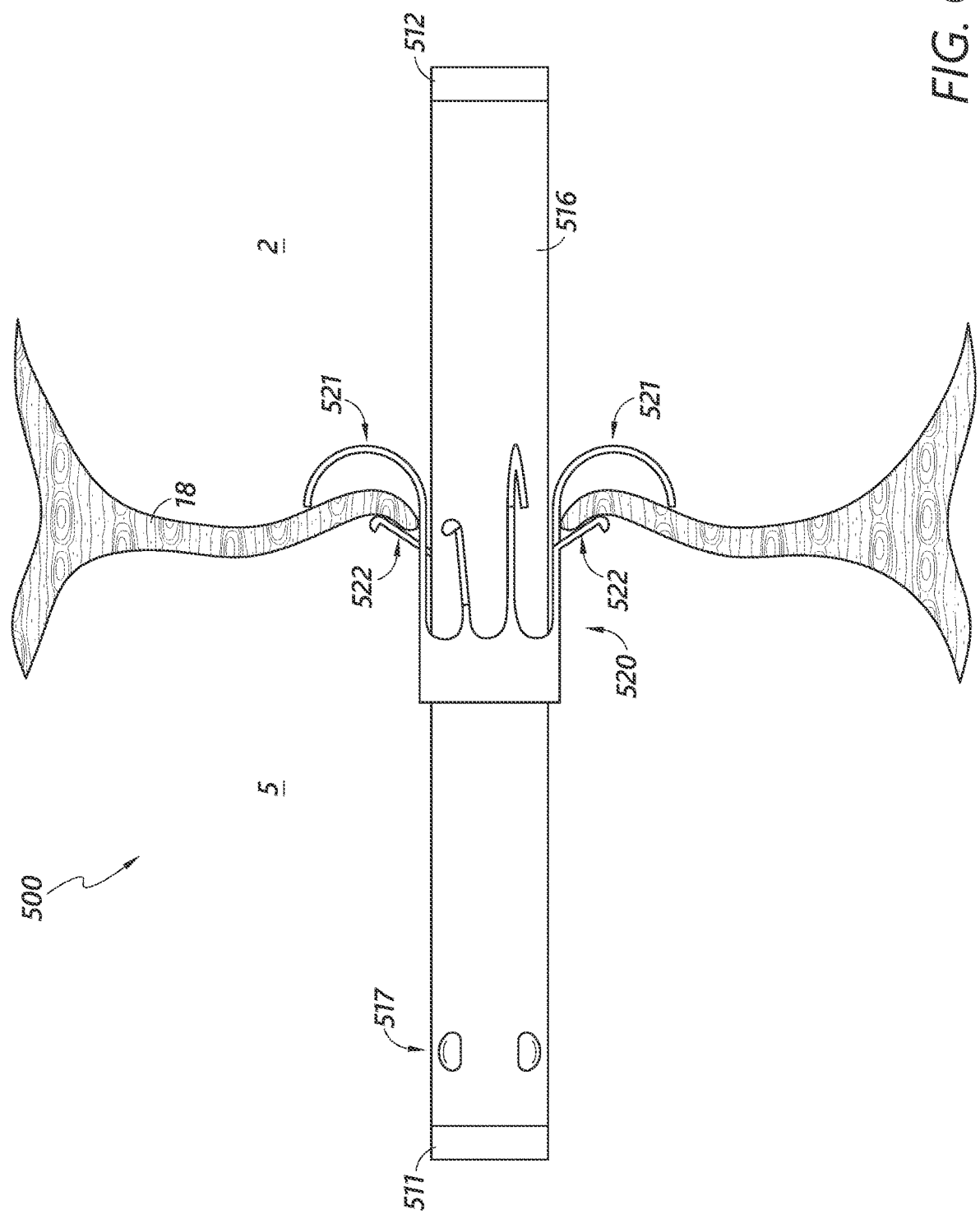
FIG. 6 shows a sensor implant device implanted in a tissue wall in accordance with one or more embodiments.

The anchor 520 may allow for direct mounting or implantation of the sensor implant device 500 in a septal wall, or other tissue. FIG. 6 shows the sensor implant device 500 implanted in a tissue wall 18, such as an interatrial septal wall. Although certain Figures and description herein are described in the context of the sensor implant device 500 implanted in an interatrial septal wall, it should be understood that the sensor implant device 500 may be implanted in any biological tissue or tissue wall in accordance with embodiments the present disclosure.

In some embodiments, the sensor implant device 500 comprises a proximal sensor element 511 and a distal sensor element 512, as shown. With the sensor implant device 500 implanted in the septal wall 18, each of the proximal and distal sensor elements may be disposed in a respective atrium. For example, with respect to the orientation of the illustrated embodiment of FIG. 6, the proximal sensor element 511 may be disposed in the right atrium, while the distal sensor element 512 may be disposed in the left atrium 2.

The anchor 520 may comprise any number of distal and/or proximal arms. The distal arms 521 may be curved such that end portions thereof point at least partially in a proximal direction in a deployed configuration. The proximal arms 522 may be at least partially straight and may be at least partially deflected away from a longitudinal axis of the sensor device and/or the sensor device itself and project at least partially in a distal direction. Furthermore, end portions of the proximal arms 522 may be at least partially curved, rounded, or otherwise configured to provide a blunt surface for contacting the tissue wall surface to reduce risk of tissue damage.

The anchor 520 is illustrated as having three or more distal arms and three or more proximal arms. In some embodiments, the anchor 520 may comprise four or more proximal arms and four more distal arms in some embodiments. In some embodiments, the sensor implant device 500 has a size that is sufficiently small to not preclude future crossing of the septal wall for alternative interventions once implanted.

In some embodiments, the sensor 510 comprises a rigid housing, which may be made of glass or other at least partially rigid material. The projection feature(s) 517 may be made of the same material as the housing 516 of the sensor 510. For example, where the housing 516 comprises a cylindrical glass tube, the projection features 517 may be projections thereof that are a unitary form with the housing 516. Alternatively, the projection feature(s) 517 may be attached or secured to the housing 516 in any suitable or desirable manner.

Generally, where the sensor housing 516 comprises glass, the sensor 510 may have desirable biocompatibility and/or outgassing prevention characteristics. For example, with respect to certain materials as used for the sensor housing 516, outgassing may occur at least in part through the housing 516, such as from internally-disposed electronics of the sensor 510, or the like. The housing 516 advantageously provides a sufficient hermetic barrier seal for the sensor 510 and/or internal circuitry or components thereof. In some embodiments, the anchor 520 comprises a memory metal frame, such as Nitinol or the like. The anchor 520 may be secured to the sensor 510 through a friction fit, or using any other suitable or desirable attachment mechanism, including biocompatible adhesive, welding, or other attachment mechanism.

FIG. 7 is a flow diagram illustrating a process 700 for implanting a sensor implant device in accordance with one or more embodiments of the present disclosure. FIG. 8 illustrates states of components of a sensor implant device and/or an associated delivery system corresponding to the various steps of the process 700 of FIG. 7. Although FIGS. 7 and 8 relate to implantation of a sensor implant device in a septal wall, it should be understood that initial puncture of the septal wall and/or dilation thereof (e.g., using a balloon or other mechanism) that may be used to create an aperture in the septal wall for insertion or implantation of a delivery catheter and/or sensor implant device is not shown or described in detail.

In connection with the steps of the process 700, access to the target implantation location may be achieved in any suitable or desirable way. For example, access to the right atrium may be made via the femoral vein in some implementations. At block 702, the process 700 involves introducing a delivery catheter 730 into the left atrium through an aperture in the septal wall 18. At block 704, the process 700 involves advancing an internal pusher or ejector component (not shown) of the delivery catheter 730 to thereby deploy or eject a distal portion of a sensor implant device 700 out of a distal end of the delivery catheter 730, as shown at state 802 of FIG. 8. The sensor implant device 700 may comprise one or more distal anchor arms 721, which may be similar to the distal arms 521 shown in FIGS. 5 and 6. Further in connection with block 704, the process 700 may involve ejecting the sensor device 700 from the delivery catheter 730 just enough to expose the distal arms 721, but not enough to eject from the delivery catheter proximal arms associated with the sensor implant device.

With the distal arms 721 ejected from the delivery catheter 730, the process 700 involves, at block 706, retracting the delivery system to set the distal arms 721 against the septal wall 18, as shown at state 803 of FIG. 8. For example, the distal end 731 of the delivery catheter 730 may be drawn back into the right atrium 5 to set the distal arms 721 against the left atrium side of the septal wall 18 in accordance with some implementations. Once the distal arms 721 have been set against the septal wall, the process 700 may involve, at block 708, further retracting the delivery system 730 to deploy proximal arms 722 of the anchor 720 associated with the sensor implant device 700 against the right atrium side of the septal wall 18. Retraction of the delivery catheter 730 to expose the proximal arms (e.g., Nitinol arms), which may thereafter engage the right side of the septal wall 18 with respect to the illustrated orientation of the septal wall. In some implementations, the distal arms 721 and/or proximal arms 722 may be configured or formed to provide tension against the septal wall 18 when the sensor implant device is fully deployed as shown at state 804 of FIG. 8. In some implementations, the distal arms 721 may have a curved form or shape, as shown herein, whereas the proximal arms 722 may comprise an at least partially straight form or shape.

With the sensor implant device 700 implanted as shown at state 804 of FIG. 8, the sensor element 712 may be deployed in the left atrium 2 and configured to provide pressure or other readings associated therewith. In some embodiments, an additional sensor element 711 associated with a proximal end or portion of the sensor 710 may be disposed in the right atrium 5 and may be used to provide pressure or other physiological parameter measurements associated with the right atrium 5, which may be used for differential pressure measurements and/or other measurements.

Figure 9:
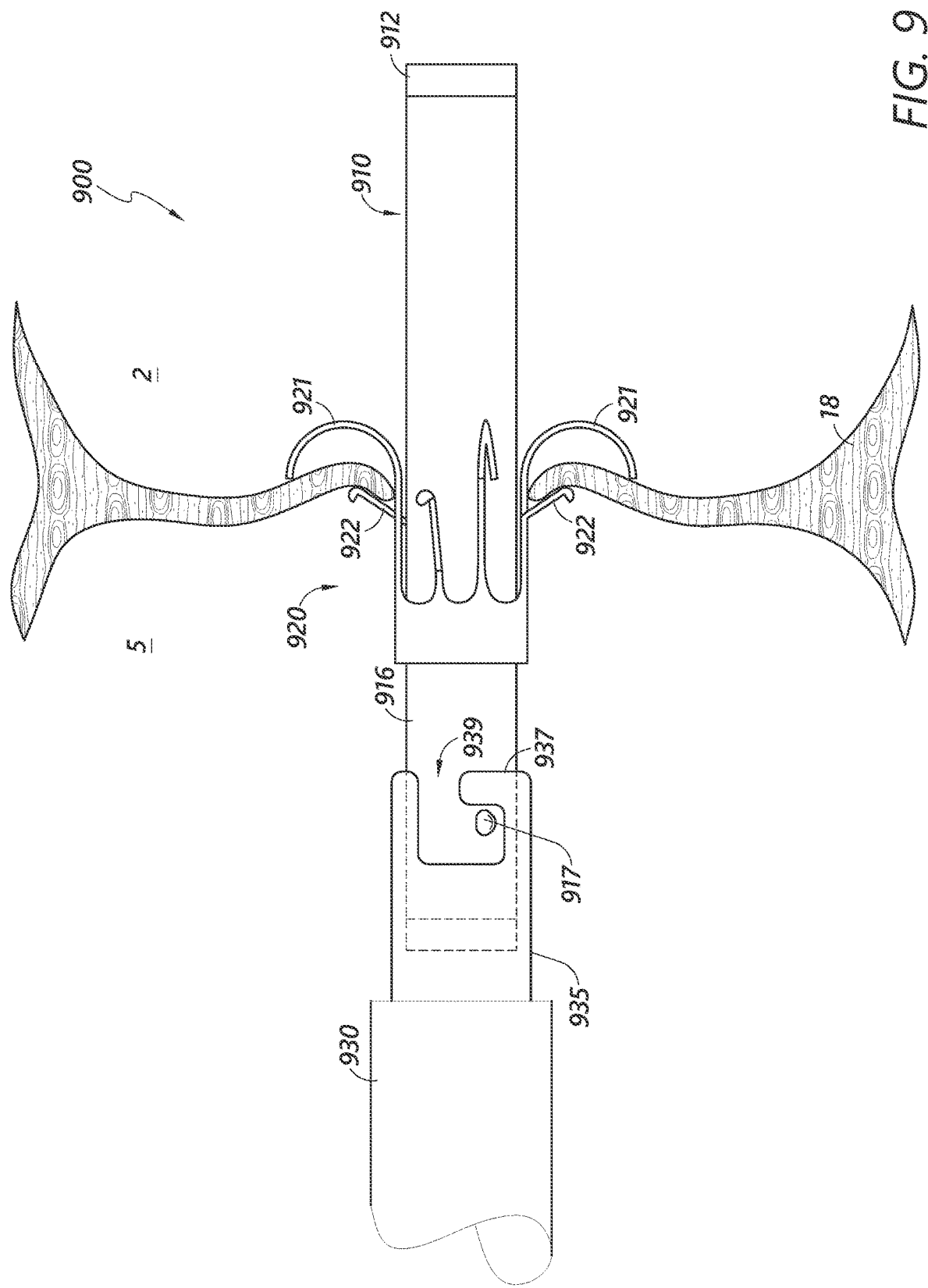
FIG. 9 illustrates a system for removing a previously-implanted sensor implant device in accordance with one or more embodiments.

In some embodiments, sensor implant devices in accordance with the present disclosure may be configured, shaped, and/or designed to facilitate recapture or removal of the sensor implant device. FIG. 9 illustrates a system for removing a previously-implanted sensor implant device 900 in accordance with one or more embodiments. The system of FIG. 9 includes a delivery/extraction catheter 930, which may be used to deliver and/or remove or extract the sensor implant device 900. The system further includes a pusher or extraction device 935, which may be movable within the delivery catheter 930 in some embodiments.

As described in detail herein, a sensor device 910 may include one or more projections 917 or other engagement features to facilitate engagement of the sensor device 910 for implantation and/or extraction. In some embodiments, the pusher/extraction device 935 comprises a projection engagement feature 937. For example, the pusher/extraction device 935 may have an at least partially hollow cylindrical form configured and dimensioned to fit at least partially around the sensor 910, wherein a gap 939 of the engagement feature 937 of the pusher/extraction device 935 allows for the pusher/extraction device 935 to be passed longitudinally past the projection feature 917, wherein rotation of the pusher/extraction device 35 allows for the engagement feature (e.g., extension member) 937 to circumferentially overlap the projection feature 917. With the pusher/extraction device 935 rotated as shown in FIG. 9, retraction of the pusher/extraction device 935 may cause the sensor implant device 900, or the sensor 910 component thereof, to be drawn toward the direction of the right atrium. Therefore, the pusher/extraction device 935 may provide a bayonet-style engagement mechanism that may be selectively engaged with, and released from, the projection feature 917. Although a single projection feature 917 is shown in FIG. 9, it should be understood that the sensor implant device 900 may have any number of projection features, and further the pusher/extraction device 935 may have any number of respective projection engagement features.

In some embodiments, the shape or form of the distal arms 921 of the anchor 920 may allow for the arms to be pulled into a more straightened configuration/form to allow for the anchor 920 to be pulled or drawn through the aperture in the septal wall 18. Therefore, by further retracting the delivery catheter 930 and/or extraction device 935 in the illustrated direction, the sensor implant device 900 may be removed from its implanted location in the septal wall 18. The shape of the distal 921 and proximal 922 arms of the anchor 920 may facilitate the recapture of the anchor 920. Recapture/removal of the sensor implant device 900 may be performed interprocedurally, or at a later time, should the need or desire arise.

Although the pusher/extraction device 935 is described in respect to removal of the sensor implant device 900 and/or sensor component 916, the pusher/extraction device 935 may be utilized to implant the sensor implant device 900 and/or sensor component 916 in some embodiments. For example, the pusher 935 may be used to manipulate the implant device 900 as it is deployed. When used for deployment, the pusher device 935 may push the sensor projection feature 917 to engage the sensor implant device 900 and the septal wall as shown, after which the pusher device 935 may be rotated to disengage the engagement feature 937 from the projection feature 917 to allow for withdrawal of the pusher device 935 away from the sensor implant device 900.

Figure 10:
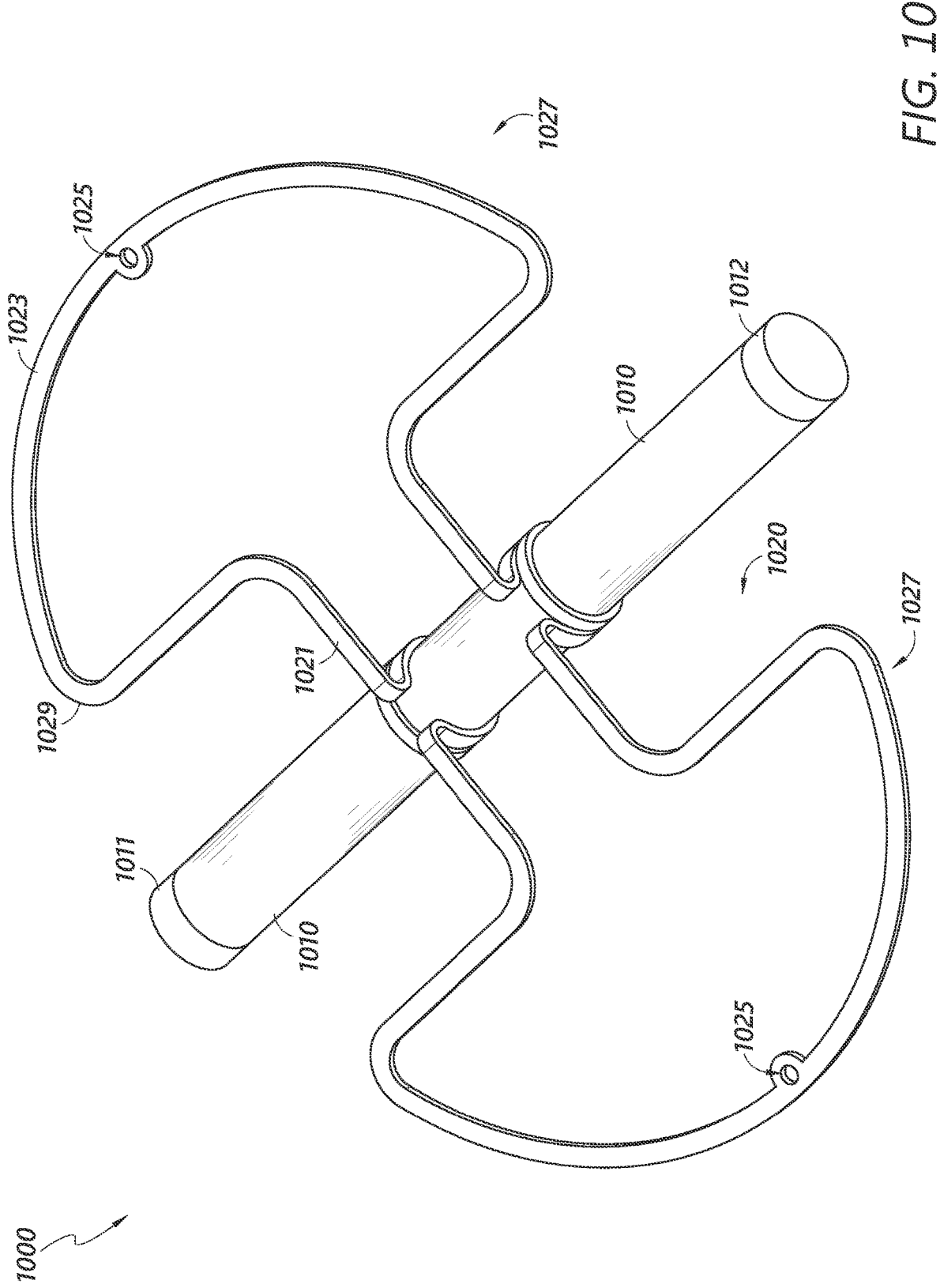
FIG. 10 illustrates a sensor implant device in accordance with one or more embodiments.

FIGS. 5-9 illustrates a sensor implant device having an anchor with a particular configuration comprising distal and proximal arms, as described above. FIG. 10 illustrates a sensor implant device 1000 having an anchor 1020 having a different form and/or configuration than that described above. In particular, the anchor 1020 of the sensor implant device 1000 shown in FIG. 10 may allow for implantation of a sensor 1010 in a chamber or vessel associated with a heart or other anatomy, such as within the left atrium of the heart, wherein the entirety of the sensor device 1010 is disposed in a single vessel or chamber, whereas arms 1027 of the anchor 1020 are primarily maintained in a chamber or vessel opposite the tissue wall separating the sensor 1010 from the anchor arms 1027.

Figure 11:
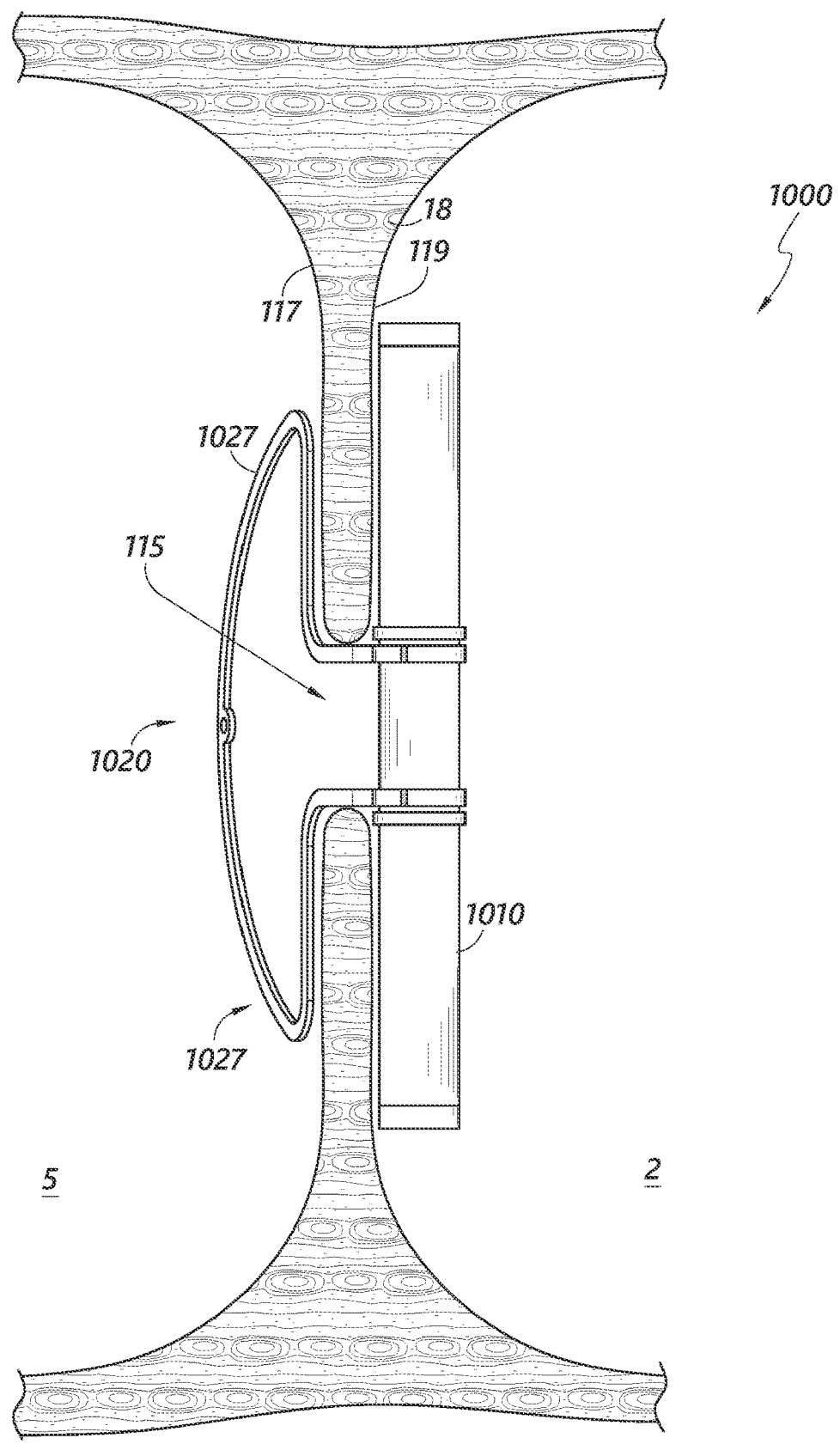
FIG. 11 shows a sensor implant device in accordance with one or more embodiments.

FIG. 11 shows the sensor implant device 1000 implanted in a septal wall 18. In some embodiments, a cylindrical or other-shaped sensor 1010 is used as an anchoring member when implanting the sensor implant device 1000 in the desired tissue wall. As implanted, the anchor arms 1027 may serve to hold the sensor 1010 against a first side 119 of the septal wall 18 at least in part by applying pressure or force on an opposite side 117 of the septal wall 18. As implanted, therefore, the sensor 1010 may be held relatively close to the septal wall 18. With the sensor disposed and secured in the chamber 2 (e.g., left atrium), sensor elements thereof may be used to detect pressure or another physiological parameter in the chamber 2. Although FIG. 11 shows the sensor 1010 disposed in the left atrium 2, in some embodiments, the sensor may be disposed in the right atrium 5, or other vessel or chamber, whereas the anchor arms 1027 may be primarily disposed within the left atrium 2. In some embodiments, the implant device 1000 comprises an occluding membrane or cloth (e.g., polymer fiber cloth) attached to the frame of the anchor 1020 and covering at least a portion of the opening 115 in the septal wall 18.

With further reference to FIG. 10, the anchor 1020 may comprise memory metal, such as Nitinol or the like, and/or other at least partially rigid material. In some embodiments, one or more arms or features of the anchor 1020 comprise tissue or suture attachment features 1025, such as one or more eyelets, or the like. For example, once implanted, the eyelet(s) 1025 of the anchor frame 1020 may be stitched to the tissue wall to thereby secure the sensor implant device 1000 in the implanted position. Where the anchor 1020 comprises multiple eyelets or other attachment features, sutures may be run through each respective feature to provide desirable attachment. Alternatively, eyelets or other suture engagement features may be used for retrieval, movement, and/or retraction of the anchor frame 1020. For example, prior to deployment thereof, with the anchor frame 1020 disposed within a delivery catheter in a collapsed state, sutures may be engaged with each of the eyelet features 1025 shown, wherein at least one eyelet or another suture engagement feature is associated with each respective anchor arm 1027. If during placement of the sensor implant device 1000, the position of the anchor frame and/or sensor 1010 is inadequate in some way, the sutures attached to the eyelet(s) or other suture-engagement feature(s) 1025 may be pulled through the delivery catheter to thereby bring the arms 1027 into an at least partially collapsed state, which may allow for repositioning of the sensor device 1000 and/or withdrawal of the sensor implant device 1000 and/or anchor 1020 back into the delivery catheter.

The illustrated half-circle shape of the anchor arms 1027 may help secure the anchor arms 1027 with the tissue at the target location. For example, corner features 1029 of the anchor 1020 may provide desirable engagement with and/or embedding in the target tissue. Furthermore, the illustrated shape of the anchor arms 1027 may serve to allow for easy retraction and/or withdrawal of the anchor back into the delivery catheter.

In the implanted configuration of FIG. 11, tissue ingrowth may develop on one or both sides of the septal wall 18 on either or both the anchor frame arms 1027 and the sensor 1010. In some embodiments, a coating or material may be added or used in connection with the sensor 1010 that serves to inhibit tissue ingrowth thereon. Such material or coating may advantageously be such as to not substantially affect the dynamics of the sensor element(s).

Figure 12:
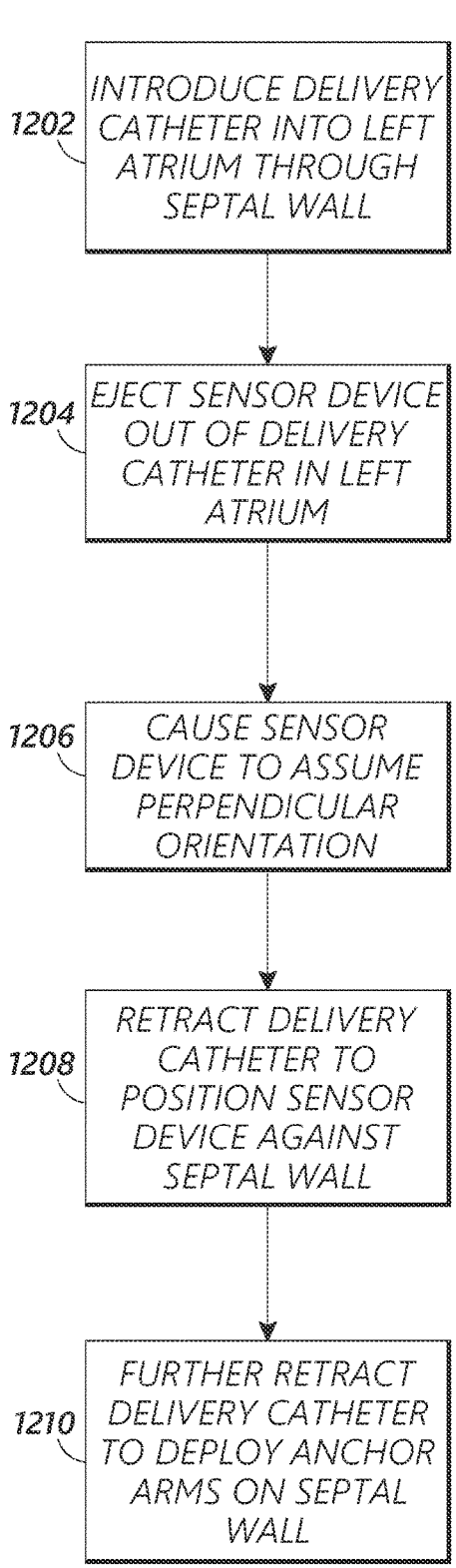
FIG. 12 is a flow diagram illustrating a process for implanting a sensor implant device in accordance with one or more embodiments.
Figure 13:
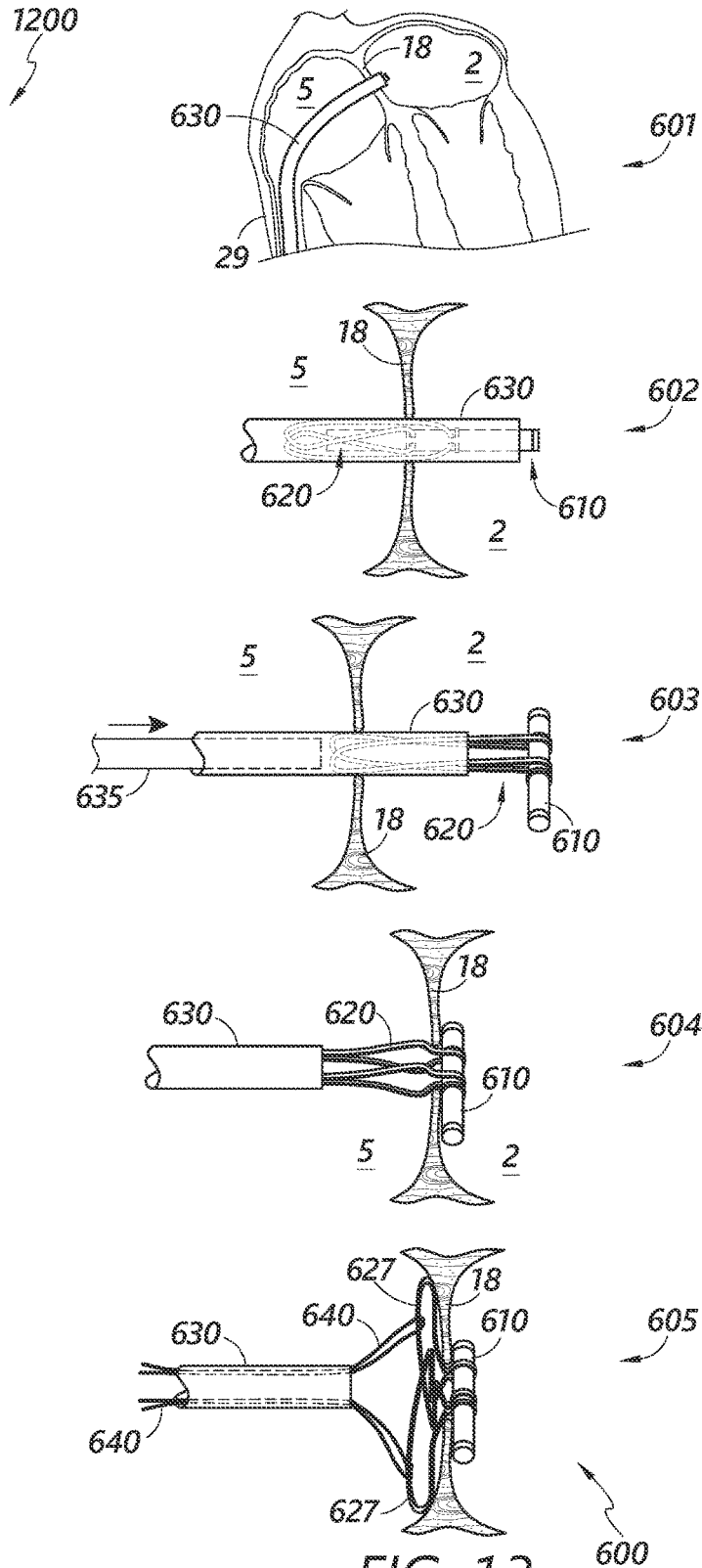
FIG. 13 illustrates states of components of a sensor implant device and/or an associated delivery system corresponding to the various steps of the process of FIG. 12 in accordance with one or more embodiments.

FIG. 12 is a flow diagram illustrating a process 1200 for implanting a sensor implant device similar in certain respects to the sensor implant device 1000 illustrated FIGS. 10 and 11 in accordance with one or more embodiments of the present disclosure. FIG. 13 illustrates the implant sensor device 600 and associated delivery system, as well as target implantation site anatomy, at various states of the process 1200.

At block 1202, the process 1200 involves advancing/introducing a delivery catheter 630 into the left atrium 2. For example, access to the left atrium 2 may be achieved through the inferior vena cava 29, right atrium 5, and through the septal wall 18 separating the right atrium 5 from the left atrium 2. Access to the inferior vena cava 29 may be achieved through the femoral vein or other access port.

With the distal end of the delivery catheter 630 disposed in the left atrium 2, the process 1200 involves, at block 1204, ejecting a sensor 610 of a sensor implant device 600 out of the delivery catheter 630. The process 1200 may advantageously first involve ejecting only the sensor element 610, while at least a portion of the associated anchor form 620 remains within the delivery catheter 630, as shown in states 602 and 603 of FIG. 13. In some embodiments, a pusher device 635 may be used to eject the sensor 610 from the delivery catheter 630.

At block 1206, the process 1200 involves causing the sensor device 610, which may be initially ejected from the delivery catheter in a longitudinally-aligned orientation with respect to the delivery catheter 630, to turn or pivot to assume an orientation that is substantially perpendicular to a longitudinal axis of the distal end of the delivery catheter 630, as shown in state 603 of FIG. 13. Although a perpendicular orientation as shown and described for the sensor 610, it should be understood that the step of causing the sensor 610 to turn or pivot may not bring the sensor into a perpendicular orientation but may merely cause the sensor 610 to assume an orientation that is more perpendicular than the coaxial orientation with the distal end of the delivery catheter. In some embodiments, the anchor frame 620 comprises memory metal (e.g., Nitinol), which may be pre-shaped to cause the sensor 610 to pivot/turn as shown. That is, the anchor frame 620 may be attached to a portion of the sensor 610, wherein after ejection from the delivery catheter 630, the shape memory characteristics of the frame cause the sensor 610 to pivot or turn as shown.

At block 1208, the process 1200 involves retracting the delivery catheter to position the sensor (e.g., pressure sensor) against the septal wall 18. The sensor 610 may thereby serve to anchor itself in the desired position against septal wall on one side thereof.

At block 1210, the process 1200 involves further retracting the delivery catheter 630 to deploy the anchor arms 627 of the anchor frame 620 on the opposite side of the septal wall 18 with respect to the pressure sensor 610. When the arms 627 have been deployed from the delivery catheter 630, they may swing outward, as shown, to contact the septal wall 18 and provide tension force to secure the implant device 600 in the desired position. For example, the frame 620 may be pre-shaped such that the arms 627 flare outward when deployed from the delivery catheter 630. In some embodiments, the anchor arms 627 have suture engagement features, such as eyelets or the like, for coupling suture(s) 640 thereto. Such suture(s) may advantageously allow for the frame arms 627 to be drawn back into a relatively straightened form for reentry into the delivery catheter 630 in the event that is desired to remove, retract, or reposition the sensor device 600. When the desired implantation position is achieved, the suture(s) may be withdrawn through the suture engagement features of the anchor arms 627 to thereby release the anchor 620 from the delivery system. Although separate sutures are shown for each of the anchor arms in FIG. 13, in some embodiments a single suture is coupled to both anchor arms.

Figure 14:
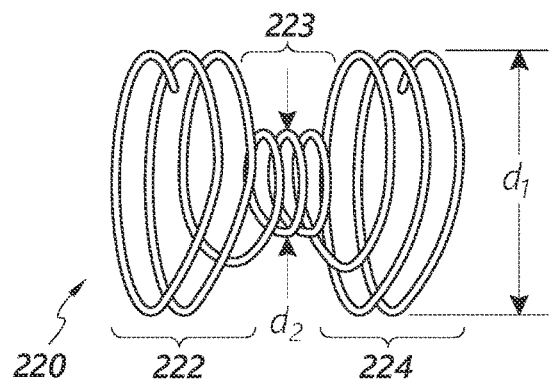
FIG. 14 illustrates a sensor anchor in accordance with one or more embodiments.

A sensor anchor in accordance with embodiments of the present disclosure may comprise a plurality of coil stacks at proximal and distal ends, with a smaller-diameter coil in between configured to engage protrusions or projections on a cylindrical sensor to secure the sensor to coil. FIG. 14 illustrates an embodiment of a sensor anchor 220 in accordance with one or more embodiments of the present disclosure. The anchor 220 comprises a wire form having a plurality of helical portions having different diameters. For example, in some embodiments, the anchor 220 comprises two large-diameter helical portions, including a proximal large-diameter portion 222 and a distal large-diameter portion 224, one or more of which may have a diameter $d_1$, as shown. The anchor 220 may further comprise an intermediate smaller-diameter helical portion 223 having a diameter $d_2$ that is less than the diameter $d_1$. The anchor wire form 220 may advantageously comprise a single unitary wire formed into the illustrated complex helical coil. Alternatively, the wire form 220 may comprise a plurality of separate wire components that are coupled or integrated to form the anchor 220.

Figure 15:
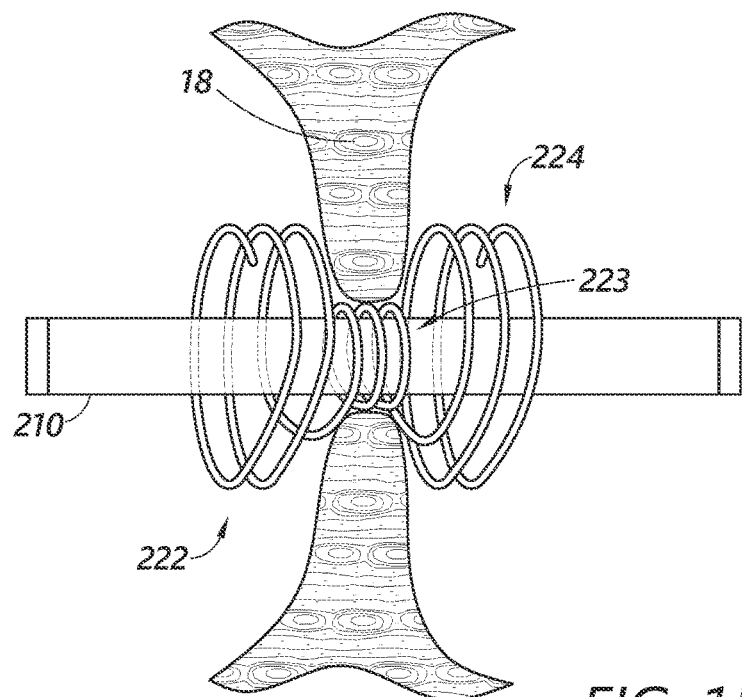
FIG. 15 shows an anchor implanted in a septal wall in accordance with one or more embodiments.

FIG. 15 shows the anchor 220 implanted in a septal wall 18, wherein the anchor 220 is engaged with a sensor device 210, such that the anchor 220 secures and anchors the sensor device 210 in the implanted position shown. For example, in some embodiments, the anchor 220 may be configured and/or dimensioned such that a cylindrical sensor device 210 may be held and secured within the smaller-diameter intermediate portion 223 of the anchor 220, whereas the distal and proximal larger-diameter portions 222, 224 may hold the implant device 200 against the septal wall 18. For example, the smaller-diameter coil portion 223 may advantageously be dimensioned to fit within an aperture/opening in the septal wall 18, whereas the larger-diameter portions 222, 224 may have a diameter larger than the septal wall opening when in an expanded form.

The anchor 220 may be delivered to the target implantation site in a delivery catheter in a compressed configuration. For example, the wire form 220 may be delivered in a substantially straightened configuration, or in a relatively-tightly wound configuration, wherein after deployment from the delivery catheter, the wire form anchor 220 is configured to assume the shape and configuration shown in FIGS. 14 and 15. In some embodiments, the anchor 220 is delivered in the delivery catheter in a configuration as wound around or attached to the sensor 210. Alternatively, the anchor may be delivered separately from the sensor. For example, the wire form anchor 220 may be implanted in the septal wall 18 as shown, after which the cylindrical sensor 210 may be pushed through the center of the one or more coils of the intermediate smaller-diameter helical portion 223 to achieve an interference fit with the smaller-diameter coil portion, such that the smaller-diameter coils are wrapped relatively tightly around the cylindrical sensor body (e.g., glass cylinder body).

Figure 16:
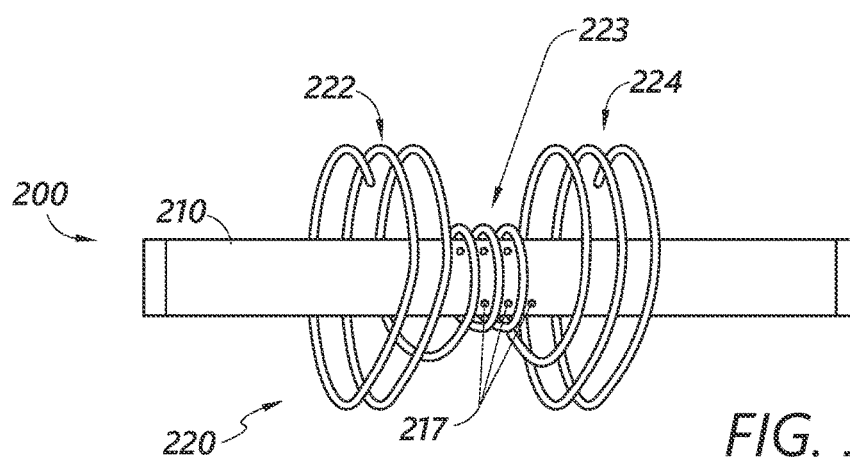
FIG. 16 illustrates a sensor anchor in accordance with one or more embodiments.

In some embodiments, the sensor 210 comprises one or more engagement features for engaging with and/or being secured to the smaller-diameter portion 223 of the anchor 220. For example, as shown in FIG. 16, the sensor 210 may comprise one or more projection features 217, as described above. Such projection features 217 may be integrated with the body of the sensor 210 or may be attached thereto using adhesive or other attachment mechanism. The projection(s) 217 may be dimensioned and/or positions such that when the projections are intertwined or pass between the coils of the smaller-diameter coil portion 223, contact between the projections and the wire coils serves to hold or maintain the sensor in a relative position with the anchor 220. In some embodiments, the projection(s) 217 are configured such that the sensor 210 may be engaged with the anchor 220 by rotating or winding the sensor through the intermediate portion 223. Therefore, removal of the sensor 210 may be achieved through unwinding the sensor 210 to disengage the projection features 217 from the smaller-diameter intermediate coils 223. Such removal may allow for access to the left atrium through the opening between the smaller-diameter coils 223. Furthermore, removal of the sensor 210 may be desirable if the sensor malfunctions or otherwise needs to be replaced or removed. In some embodiments, the wire form anchor 220 comprises memory metal wire preformed into the desired coil shape, as illustrated.

Figure 17:
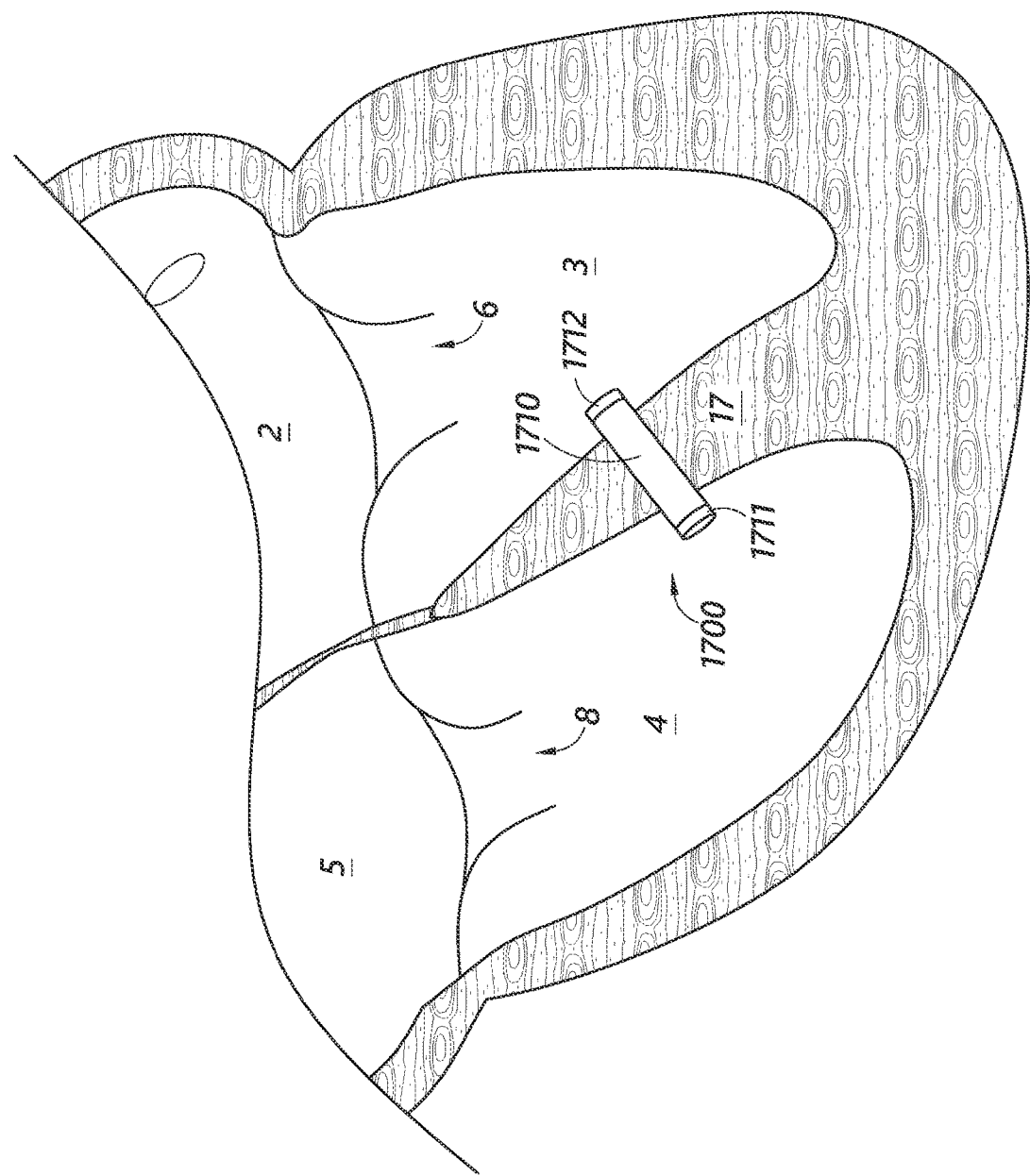
FIG. 17 shows a pressure sensor device in accordance with embodiments of the present disclosure.

Although various embodiments are illustrated in described herein in connection with sensor implant devices implanted in an interatrial septal wall, it should be understood that embodiments of the present disclosure are applicable to other implantation sites, including implantation of sensor implant devices in a ventricular septal wall. FIG. 17 illustrates an embodiment of a sensor implant device in accordance with aspects of the present disclosure. FIG. 17 shows a pressure sensor device 1710, or other type of sensor device, in a ventricular septal wall 17. The sensor implant device 1700 includes a sensor 1710 and one or more anchor features (not shown) configured to secure the sensor 1710 in the desired position in the septal wall 17.

The sensor implant device 1700 may be configured to provide sensor readings for monitoring pressure in the right ventricle 4 and/or left ventricle three. For example, the sensor 1710 may comprise one or more sensor elements 1711, 1712, each of which may be disposed in a respective ventricle of the heart 1 when implanted as shown in FIG. 17. In some embodiments, the sensor 1710 comprises only a single sensor element, and is configured to provide pressure sensor readings for only one ventricle. Ventricular pressure monitoring may be useful for diagnosing and/or treating certain heart failure patients. As is true of other embodiments disclosed herein of sensor implant devices, the sensor implant device 1700 may advantageously comprise wireless transmission functionality for receiving and/or transmitting wireless data and/or power, as described in detail herein.

Sensor-Integrated Tissue Closure Devices

Figure 18:
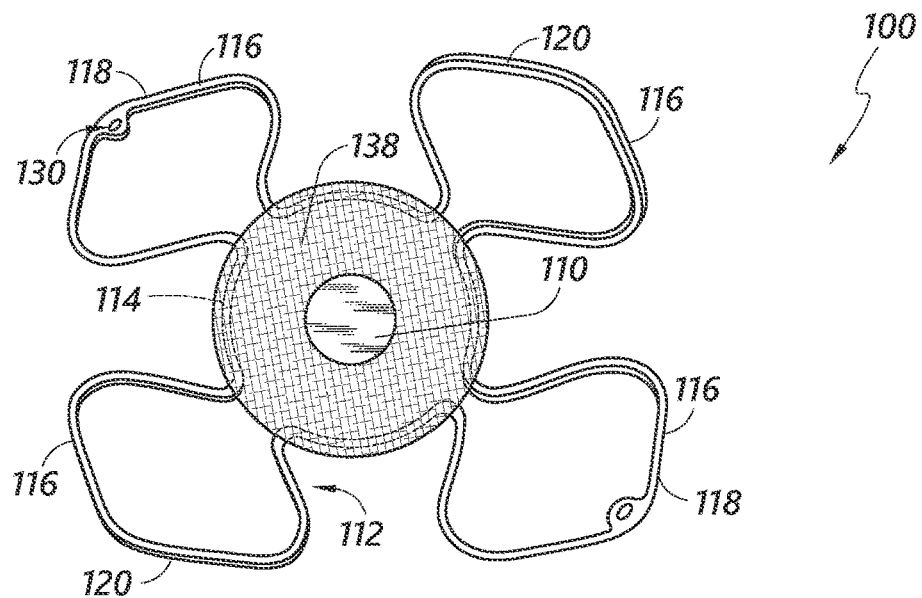
FIG. 18 shows a front view of a sensor-integrated septal-closure device in accordance with one or more embodiments.
Figure 19:
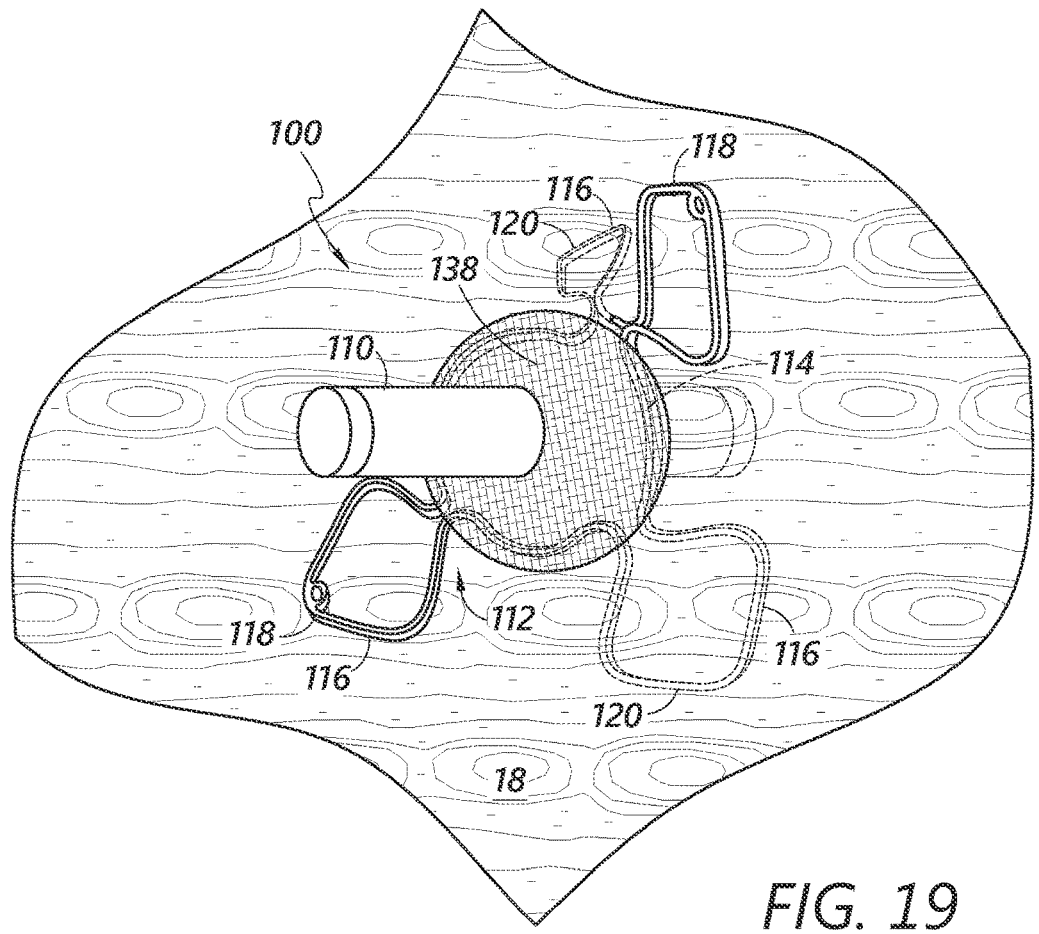
FIG. 19 shows a perspective view of the sensor-integrated septal-closure device of FIG. 18 implanted in a tissue wall in accordance with one or more embodiments.

In certain embodiments, a sensor implant device in accordance with the present disclosure may comprise a sensor integrated with a septal closure device, or other tissue closure device. Although certain embodiments are disclosed below in the context of septal closure devices, it should be understood that such disclosure is applicable to sensor-integrated implant devices comprising one or more sensors integrated with other types of tissue closure devices. FIG. 18 shows a front view of a sensor-integrated septal-closure device in accordance with one or more embodiments of the present disclosure. FIG. 19 shows a perspective view of the sensor-integrated septal-closure device of FIG. 18 implanted in a tissue wall 18. As shown in FIG. 18, a sensor-integrated septal closure device 100 can include a frame 112 configured to support a blood-occluding membrane 138. With respect to FIG. 19, the septal closure device 100 may be implanted in the septal wall 18 to close off shunts across the septal wall, which may be congenital or created during an interventional procedure. In some embodiments, a septal occluder frame and occluding membrane 138 may be implanted in the septal wall 18 first, after which a sensor device 110 may be attached to the septal closure device, such as by puncturing the occluding membrane 138 and passing the sensor device 110 therethrough.

The frame 112 in the illustrated configuration can comprise a generally planar body comprising a central portion 114 and a plurality of anchoring arms 116 extending radially outward from the central portion 114. For example, at least four arms can extend from the central portion 114, as shown in the illustrated embodiment, although the frame can have greater than four arms 116 or less than three arms 116 in other embodiments. Although arms 116 are shown and described, it should be understood that the septal closure device 100 and/or frame may include any type of tissue anchor feature(s).

The four arms 116 may include a first set of opposing arms 118 and a second set of opposing arms 120, extending from the central portion 114. The closure device desirably (although not necessarily) has the same number of arms in the first and second sets so that the clamping force exerted by the arms is evenly distributed against the septum when the device is implanted. In the illustrated embodiment, for example, the first set of arms 118 includes exactly two arms extending from opposing sides of the central occluding membrane 138, and the second set of arms 120 includes exactly two arms extending from opposing sides of the central occluding portion 138. In other embodiments, the first or second set of arms can include just one arm or more than three arms.

In a deployed or expanded configuration, the arms 116 can extend radially outwardly from the central occluding portion 138. The arms 116 can extend perpendicularly or substantially perpendicularly to a central axis of the device 100 (the central axis extending through the center of a sensor device 110 integrated with the septal closure device and perpendicular to the plane of the page) such that an atrial septum 18 can be compressed or pinched between the first set of arms 118 and the second set of arms 120 when the device 100 is implanted in a septal wall 18. In other words, when the device 110 is implanted, the first set of arms 118 can be on one side of the septal wall 18, the second set of arms 120 can be on the other side of the atrial septum, and the central portion 138 can be disposed within an opening or defect of the septum.

The frame 112 in the illustrated embodiment has a relatively thin and flat profile to avoid or minimize thrombus. Thus, to such ends, the arms 116 can be attached to a central portion of the frame 114 that is associated with an outer circumference of the central occluding membrane 138 at angularly-spaced apart locations, with the attachment locations intersecting a common plane perpendicular to the central axis; in other words, all of the arms 116 in the illustrated embodiment can be attached to the central frame portion 114 along a circumferential path defined by the central frame portion 114.

In certain embodiments, the arms 116 and the central frame portion 114 can be coplanar with each other when the device 100 is in its fully-expanded, non-deflected shape; that is, the arms 116 do not have any portions that extend axially away from the central frame portion 114. It should be understood that once implanted, the first set of arms 118 and the second set of arms 120 may be bent slightly axially away from each other by virtue of the thickness of the septum 18 and may no longer be coplanar. Nonetheless, the device 110 in certain embodiments can be said to have a flat profile with arms that are coplanar with each other and the central frame portion 114 when the device is in a non-deflected state. In other embodiments, however, the arms or portions thereof can be heat-set or otherwise shaped to extend axially away from each other or the central frame portion 114 in a non-deflected state.

The frame 112 can be radially compressed or constricted to a delivery configuration for delivery to the heart in a delivery catheter/system. For example, in the delivery configuration, the frame 112 can be placed and retained in a generally compressed configuration in which the first set of arms 118 are folded towards each other along the central axis of the device 100 and the second set of arms 120 are folded towards each other along the central axis of the device 100, such that the first and second sets of arms 118, 120, respectively, extend axially 120 and parallel to each other. When placed in the delivery configuration, the frame 112 can also be radially compressed relative to the deployed configuration.

The frame 112 can include an eyelet 130 disposed at a distal end of one or more arms for coupling the closure device 100 to the delivery system via one or more attachment sutures, as further described below. An eyelet can project towards the central portion 114, as shown in 18 and 19, or it can project away from the central portion 114.

The frame 112 can be self-expandable and can be formed from a shape-memory material, such as Nitinol, so that the frame 112 self-expands from the delivery configuration to the deployed configuration when released or deployed from a delivery apparatus. In alternative embodiments, the frame 112 can be formed from a plastically-expandable material, such as stainless steel or cobalt-chromium alloy, and can be configured to be plastically expanded from the delivery configuration to the deployed configuration by an expansion device, such as an inflatable balloon. The frame 112 can be laser cut or otherwise formed from a flat sheet of metal, such as Nitinol. Alternatively, the frame 112 can be formed by bending one or more metal wires into the form shown.

The occluding membrane 138 can be configured to block the flow of blood between the right and left atria. For an adult, the normal range of right atrial pressure is about 2-6 mmHg and the normal range of left atrial pressure is about 4-12 mmHg. Thus, throughout most of the cardiac cycle, the left atrial pressure is greater than the right atrial pressure. In some embodiments, the occluding membrane 138 can be configured to block at least the flow of blood from left atrium to the right atrium. In other embodiments, the occluding membrane 138 can be configured to block the flow of blood between the right and left atria in both directions throughout the cardiac cycle.

In particular embodiments, the occluding membrane 138 can comprise one or more sheets or pieces of material that at least partially block or impede the flow of blood through the frame 112. For example, the occluding membrane 138 can comprise one or more pieces of bioresorbable material, film or cloth that are configured to encourage tissue ingrowth and can degrade over time, leaving just regrown tissue within the central frame portion 114. For example, the occluding membrane 138 can comprise one or more pieces of bioresorbable electro-spun polymeric material, such as polylactide (PLA), polylactide glycolides (PLGA), polycaprolactone (PLC), polyacrylonitrile (PAN), poly(lactide-co-caprolactone) (PLCL), polyglyconate, and polypeptides. Compared to woven fabrics, electro-spun polymers promote faster tissue ingrowth, have faster biodegradation times, are potentially less thrombogenic, and can be created weaker and therefore can be easily punctured with a medical instrument during subsequent re-crossing of the closure device.

In some embodiments, the occluding membrane 138 can comprise one or more sheets of pieces of non-bioresorbable material, such as any of various synthetic fabrics (e.g., polyethylene terephthalate (PET)) or natural tissue (e.g., pericardium). In some embodiments, the occluding membrane 138 can be completely or substantially impermeable to blood. In other embodiments, the occluding membrane 138 can be semi-porous to blood flow (e.g., a porous fabric). The porous material can be selected to remain porous or to close-up and become impermeable or non-porous to blood over time. In a specific implementation, the occluding membrane can be made of a bio-spun polyurethane having a fiber size between approximately 0.05-1.5 microns and a porosity of between approximately 50-80%. The thickness of the occluding membrane 138 can be between approximately 100-200 microns. In another implementation, the occluding membrane can be made of a bio-spun polymer blend comprising polyurethane and PET, such as a 70/30% blend of polyurethane/PET, having similar fiber sizes and porosity. In some embodiments, the occluding membrane 38 can be made of a biocompatible foam, such as polyurethane, PET, silicone, or polyethylene foam.

The occluding membrane 138 can be configured to create a substantially fluid-tight seal with the adjacent tissue of the septum. In some embodiments, the occluding membrane 138 is configured, at least initially, to permit a small amount of blood flow between the atria to provide residual shunting. Over time, the occluding membrane 138 can promote tissue ingrowth and substantially completely close the opening in the septum and prevent residual shunting between the atria. The occluding membrane 138 can completely cover the central frame portion 114, as shown in FIGS. 18 and 19, or the occluding membrane 138 can cover a portion of the opening in the central frame portion 114. The occluding membrane 38 can be configured such that opening in the septum 18 can be accessed for reentry through the defect either before or after degradation of the occluding membrane 138.

The occluding membrane 138 can be attached to the frame 112 via heat staking, sutures, molding, bonding, weaving and/or other means known to those skilled in the art with the benefit of the present disclosure. For example, the outer edges of the occluding membrane 138 can be folded over the central frame portion 114 and then welded to a more central area of the occluding membrane 138 to fix the occluding membrane 138 to the frame 112. The occluding membrane 138 may extend beyond the periphery of the central frame portion 114, for example up to 2 mm. In some embodiments, the occluding membrane 138 may have a generally circular shape prior to attachment to the frame 112.

The occluding membrane 138 may advantageously comprise relatively thin cloth, which may be penetrated to gain access to the left atrium should the need arise in connection with future interventions. Furthermore, the frame 112 may advantageously be configured to stretch open to accommodate relatively large-diameter catheters, such that access to the left atrium through the frame 112, and particularly through the center frame portion 114, may be made.

As referenced above, the implant device 100 of FIGS. 18 and 19 includes a sensor device 110 attached to or otherwise integrated with the occluding membrane 138. The sensor device 110 may be a pressure sensor including one or more sensor elements, as described herein. For example, the sensor device 110 may have a generally cylindrical shape, and may penetrate through the occluding membrane 138, such that distal and proximal end portions of the sensor 110 are exposed on opposite sides of the septal closure device 100.

Removal of the sensor device 110 after implantation may allow for access through the occluding membrane 138 to access the left atrium. For example, the frame 112 of the septal closure device 100 may comprise memory metal or other material that is relatively easily deformed to allow passage of interventional devices. In some implementations, interventional devices may be passed through the occluding membrane 138 with the sensor device 110 remaining disposed therein or integrated therewith. In some implementations, the sensor-integrated implant device 100 may be delivered with the sensor 110 already integrated with the septal closure device.

Figure 20:
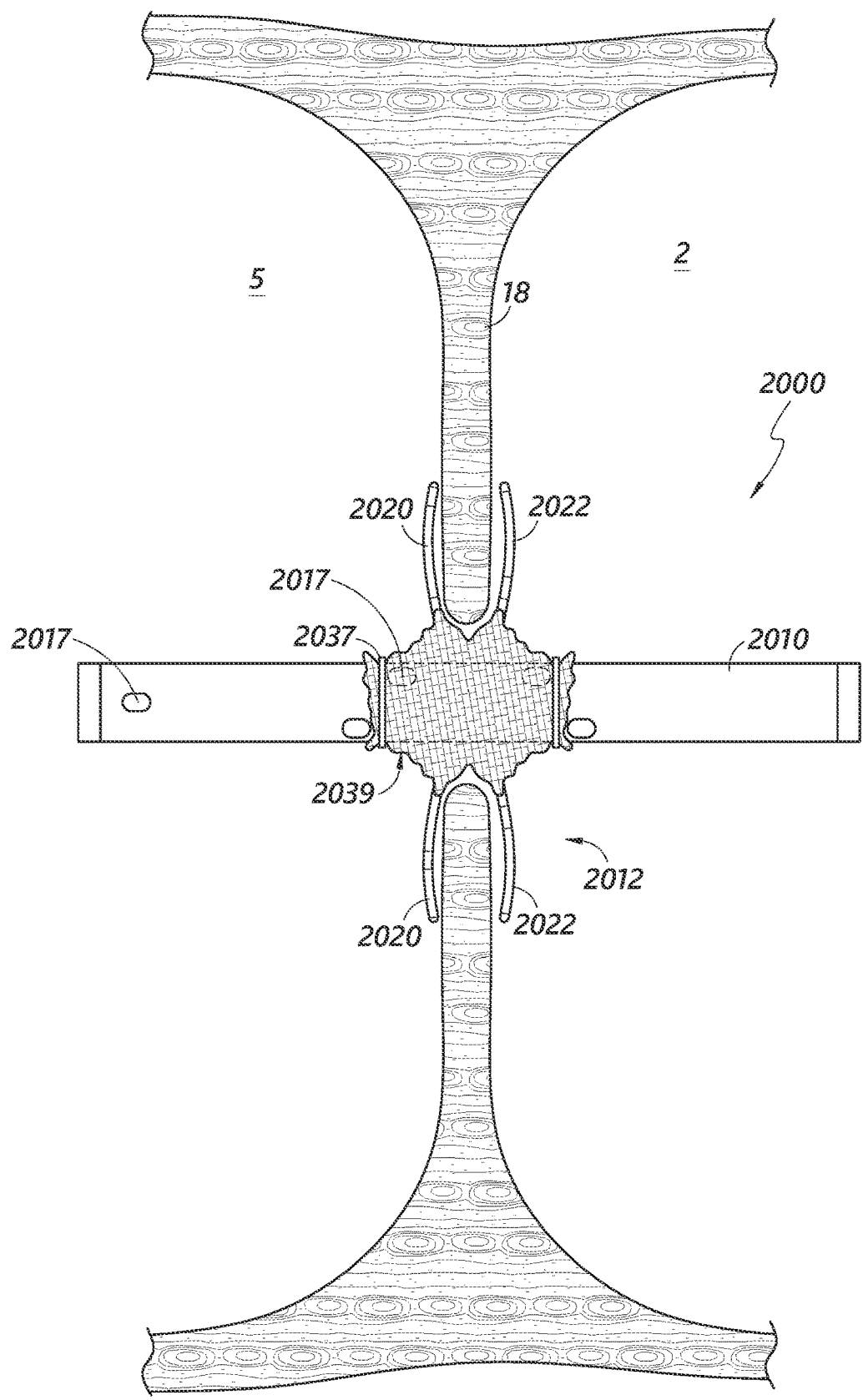
FIG. 20 illustrates a sensor implant device comprising a sensor integrated with a septal closure device in accordance with one or more embodiments.

FIG. 20 illustrates a sensor implant device 2000 comprising a sensor 2010 integrated with a septal closure device. The septal closure device comprises an occluding cloth or membrane 2038 connected to a frame 2012 comprising a plurality of arms, as described in detail herein. In order to maintain the intended function of the sensor-integrated implant device 2000, embodiments disclosed herein utilize a means for affixing the sensor 2010 to the septal closure implant. In some embodiments, the occluding membrane 1038 may comprise a cloth (e.g. bio-spun polymer cloth) membrane that is formed into one or more sleeves/cuffs 2039 that are shaped to hold the sensor device 2010. For example, with respect to a cylindrical sensor device 2010, the sleeve/cuff 2039 may be at least partially cylindrical and may serve to affix the cylindrical sensor 2010 to the frame 2012. The sleeve/cuff 2039 of the occluding membrane/cloth 2038 may be secured to the sensor device 2010 using a suture collar 2037, which may be wrapped around the sleeve/cuff 2039 and sensor device 2010 to secure the sleeve/cuff 2039 to the sensor device 2010

As described above, the occluding membrane 2038 may comprise bio-spun polymer, which may be made in any suitable or desirable geometry, such as a fabric or scaffold geometry. In some embodiments, the occluding membrane 2038 is configured to gradually become integrated with biological tissue through tissue ingrowth over time. Such membrane may advantageously be of such a nature that forces required to penetrate the membrane are less than an amount of force required to dislodge the frame 2012 from the implantation position/site. In some embodiments, as described in detail herein, the sensor device 2010 comprises one or more projection features 2017, which may be integrated forms with the body of the sensor 2010, or may be attached or adhered using biocompatible adhesive, or other attachment means.

Figure 21:
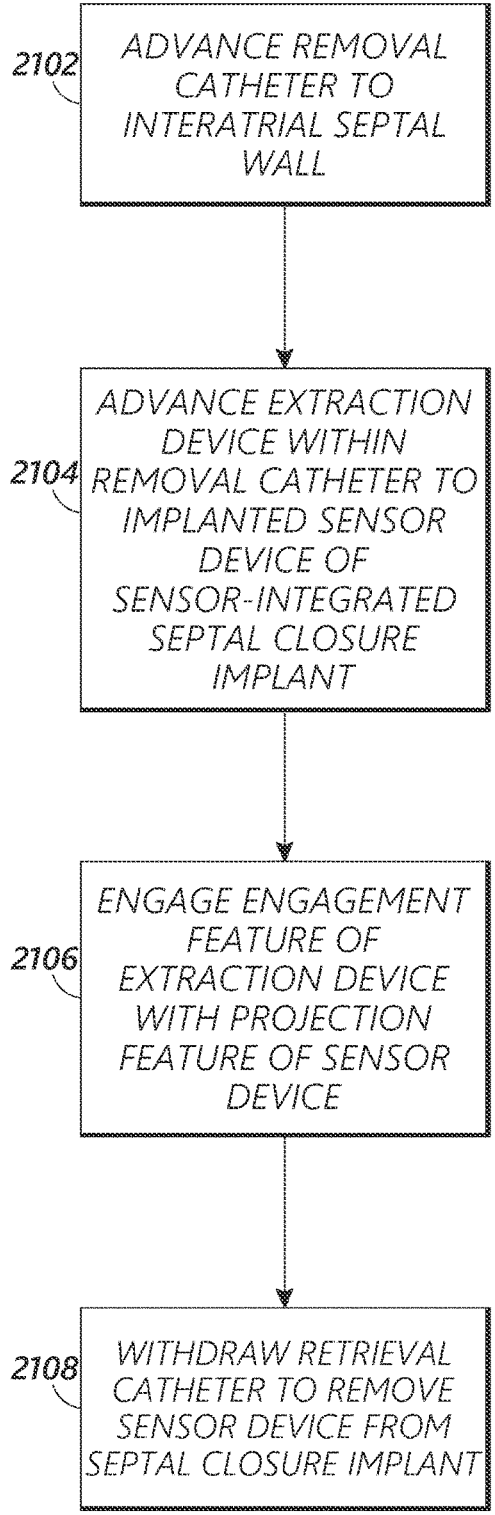
FIG. 21 illustrates a process for removing a sensor implant device in accordance with embodiments.
Figure 22:
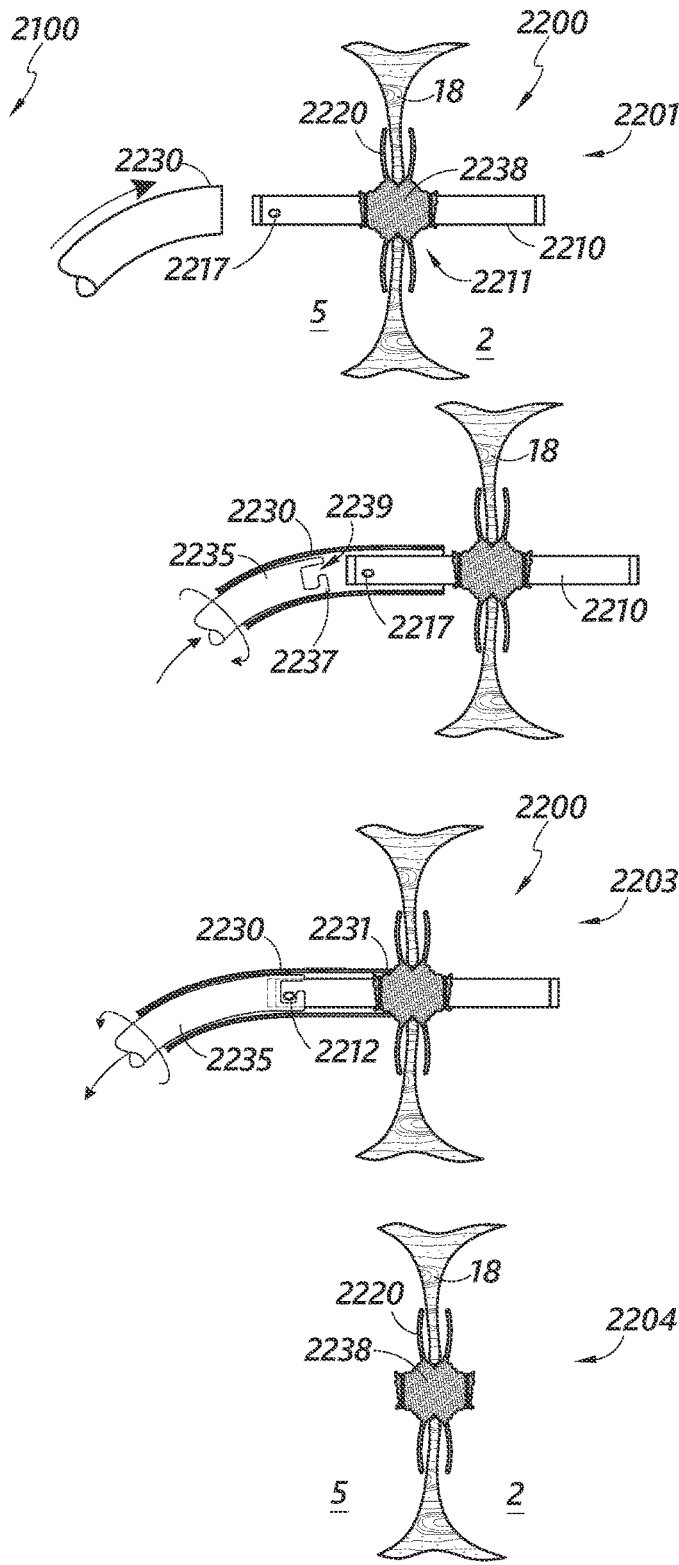
FIG. 22 illustrates a sensor implant device and associated removal system, as well as cardiac anatomy at various states corresponding to the process steps of FIG. 21.

In order to maintain the ability to gain access to the left atrium after implantation of a sensor-integrated septal closure device as described herein, a sensor implant device removal catheter may be utilized. FIG. 21 illustrates a process 2100 for removing a sensor implant device in accordance with embodiments of the present disclosure. FIG. 22 illustrates a sensor implant device and associated removal system, as well as cardiac anatomy at various states corresponding to the process steps of FIG. 21. At block 2102, the process 2100 involves introducing a removal catheter 2103 a right ventricle and advancing the removal catheter to the interatrial septal wall 18 in which a sensor implant device 2200 is implanted. The removal catheter 2230 may be used to safely remove the cylindrical sensor 2210 from the septal closure device with which it is integrated, or to remove the entire sensor-integrated septal closure device 2200. The sensor 2210 may advantageously comprise one or more protrusions or other engagement features 2217, which may be used to remove the sensor 2210. The protrusion feature(s) 2217 may radially-project from the outer surface of the sensor body 2210. Although protrusion features are described herein, it should be understood that other means of holding or grasping onto the sensor 2210 may be implemented in accordance with embodiments of the present disclosure.

At block 2104, the process 2100 involves advancing an extraction device 2235 within the retrieval catheter 2230. In some embodiments, the pusher/extraction device 2235 comprises a projection engagement feature 2237. For example, at block 2106, the process 2100 involves engaging the engagement feature 2237 with the projection feature 2217 of the sensor 2210, as shown in state 2203 of FIG. 22. The pusher/extraction device 2235 may have an at least partially hollow cylindrical tube form configured and dimensioned to fit at least partially around the sensor 2210, wherein a gap 2239 of the engagement feature 2237 of the pusher/extraction device 2235 allows for the pusher/extraction device 2235 to be passed over the projection feature 2217 in a longitudinal direction, wherein rotation of the pusher/extraction device 2235 allows for the extension/engagement feature 2237 to circumferentially overlap the projection feature 2217 to provide engagement therewith.

At block 2108, the process 2100 involves withdrawing the retrieval catheter 2230 to thereby remove the sensor 2210 from the septal closure implant 2211. For example, with the pusher/extraction device 2235 rotated as shown in state 2203 of FIG. 22, retraction of the pusher/extraction device 2235 may cause the sensor 2010 and/or septal closure implant device 2200 to be drawn toward the direction of the right atrium. Therefore, the pusher/extraction device 2235 may provide a bayonet-style engagement mechanism that may be selectively engaged with or released from the projection feature 2217. Although a single projection feature 2217 is shown in FIG. 22, it should be understood that the sensor implant device 2200 may have any number of projection features, and further the pusher/extraction device 2235 may have any number of respective projection engagement features. In some embodiments, when the pusher/extraction device 2235 is engaged with the projection feature 2217, the distal end 2231 of the of the removal catheter 2230 may be held against the septal closure device 2200 to prevent dislodgment of the septal closure device 2200 during extraction of the sensor 2210.

State 2204 of FIG. 22 shows the septal closure implant device 2200 with the sensor device 2210 removed therefrom. However, it should be understood that in certain embodiments the entire sensor-integrated septal closure device 2200 may be removed in connection with the process 2100. Once the sensor 2210 is removed from the septal closure device 2200, the relatively weak occluding membrane 2238 (e.g. bio-spun polymer) may be relatively easily crossed using standard device catheters.

Although the pusher/extraction device 2235 is described with respect to removal of the sensor implant device 2200, the pusher/extraction device 2235 may be utilized to implant the sensor implant device 2200 in some embodiments. For example, the pusher 2235 may be used to manipulate the implant device 2200 as it is deployed. When used for deployment, the pusher device 2235 may push the sensor projection feature 2217 to engage the sensor implant device 2200 and the septal wall as shown, after which the pusher device 2235 may be rotated to disengage the engagement feature 2237 from the projection feature 2217 to allow for withdrawal of the pusher device 2235 away from the sensor implant device 2200.

Additional Sensor-Integrated Cardiac Implant Devices

Figure 23:
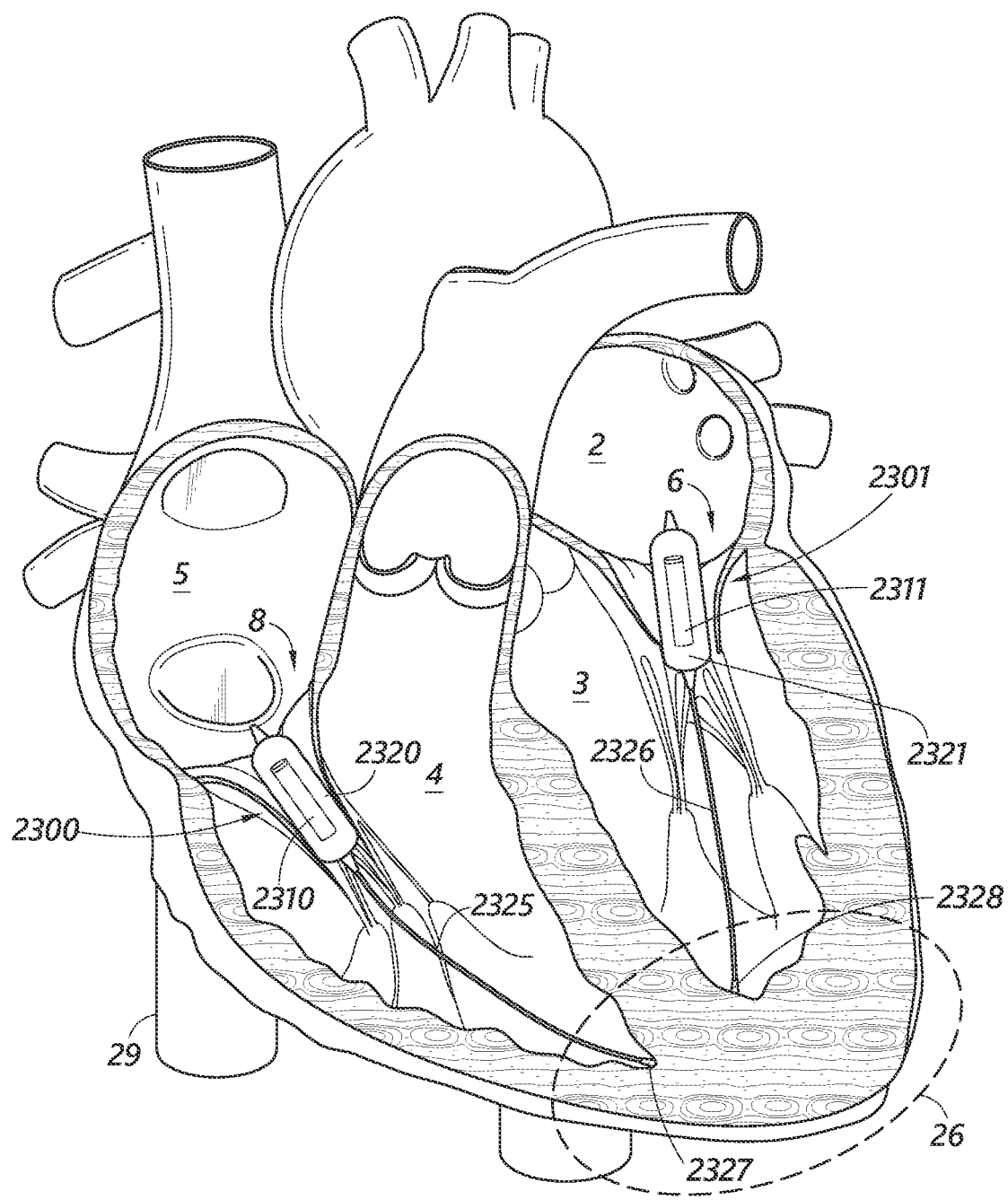
FIG. 23 illustrates a sensor implant device comprising a sensor integrated with a heart valve spacer device in accordance with one or more embodiments.

In certain embodiments, a sensor implant device may comprise a sensor integrated with a heart valve spacer device. As shown in FIG. 23, a valve spacer device 2300, 2301 may be implanted in a heart 1 to improve competency of the tricuspid valve 8 or the mitral valve 6. Although the description below focuses on the sensor-integrated spacer implant device 2300, which is implanted in the right ventricle 4 and positioned to fit within the tricuspid valve 8 to improve competency thereof, it should be understood that the description below is applicable to sensor-integrated spacer implant devices implanted in any valve and/or in the left ventricle as well. This spacer implant device 2300 may be designed to reduce valve regurgitation by occupying a regurgitant orifice area between the native valve leaflets and providing a surface for leaflet coaptation. The sensor-integrated spacer implant device 2300 consists of a spacer form 2320 and a tether 2325 that is anchored in the right ventricle 4, such as at or near the ventricular apex 26. The spacer form 2320 may comprise an at least partially filled polymer (e.g., foam-filled) balloon that is configured to passively expand via one or more openings in the spacer chamber. The openings into the spacer form 2320 may be positioned at opposite longitudinal ends of the spacer form in some embodiments. The openings in the spacer form 2320 may allow for the spacer form 2320 to be compressed for catheter-based deliverability. In some embodiments, the spacer implant 2300 includes one or more radiopaque markers to help in positioning the spacer using fluoroscopy. The spacer form 2320 may have any suitable or desirable size, such as approximately 12 mm or 15 mm in diameter, with a length of approximately 42 mm, or any other dimensional values.

In some embodiments, the implant device 2300 is fixed at a distal end in the right (or left) ventricular myocardium using a tissue anchor 2327. The tissue anchor 2327 may have any suitable or desirable form. For example, in some embodiments, the anchor 2327 comprises a pronged metal anchor that is designed to minimize the risk of penetration of the epicardial surface and/or prong exposure in the ventricle. In some embodiments, the implant device 2300 may comprise excess device length (not shown) that extends through the right atrium 5 and into a subcutaneous pocket (not shown). In some embodiments, one or more of an antenna and/or wireless communication chip and/or circuitry may be contained within the subcutaneous pocket. Such antenna and/or circuitry may be configured to wirelessly communicate and/or process data and/or power relating to sensor functionality of the implant device 2300.

The filling of the spacer form 2310 may comprise elastomeric foam in some embodiments, which may provide suitable or desirable compression and decompression characteristics. The implant device 2300 includes a sensor 2310, which may be integrated with the spacer form 2320 in any suitable or desirable way. For example, in some implementations, the spacer form 2320 includes an exterior slot or recess in the exterior spacer form and/or the internal foam or chamber. The sensor 2310 may be configured and/or positioned within the implant device 2300 such that the sensor element is positioned to determine pressure readings in the ventricle 4 and/or the atrium 5. In embodiments in which the sensor 2310 is disposed within the exterior balloon form of the spacer 2320, a pressure sensor diaphragm of sensor 2010 may protrude at least partially from the spacer form 2320 such that the pressure sensor diaphragm may be used to determine fluid pressure external to the spacer form 2320.

In some embodiments, the spacer form 2320 is fluid-filled, such that fluid pressure external to the spacer form 2320 is at least partially transferred, or translates in some manner, to fluid pressure within the spacer form. In some embodiments, the internal pressure of the spacer form 2320 provides information indicating how hard the valve leaflets strike the spacer form during cardiac cycles. That is, in some embodiments, the sensor 2310 is configured to measure pressure in one or more chambers of the heart 1, as well as leaflet contact force on the spacer form. Leaflet contact force may be measured to determine functional wear of the implant device 2300. In some embodiments, the spacer form 2320 has one or more openings at one or more longitudinal ends thereof through which a sensor element may be exposed to external fluid pressure.

In some embodiments, a battery or other power source is maintained within the 2320. Furthermore, wireless transmission and/or control circuitry may be contained within the 2320 and/or sensor 2310, including one or more antennas, chips, conductors, and/or the like. Such components and circuitry may be configured to wirelessly communicate and/or process data and/or power relating to sensor functionality associated with the sensor 2310. In some embodiments, the sensor-integrated implant 2300 is configured to provide atrial pressure readings, as well as pressure readings relating to pulmonary artery pressure, which may provide information that describes both valve and ventricular performance.

Figure 24:
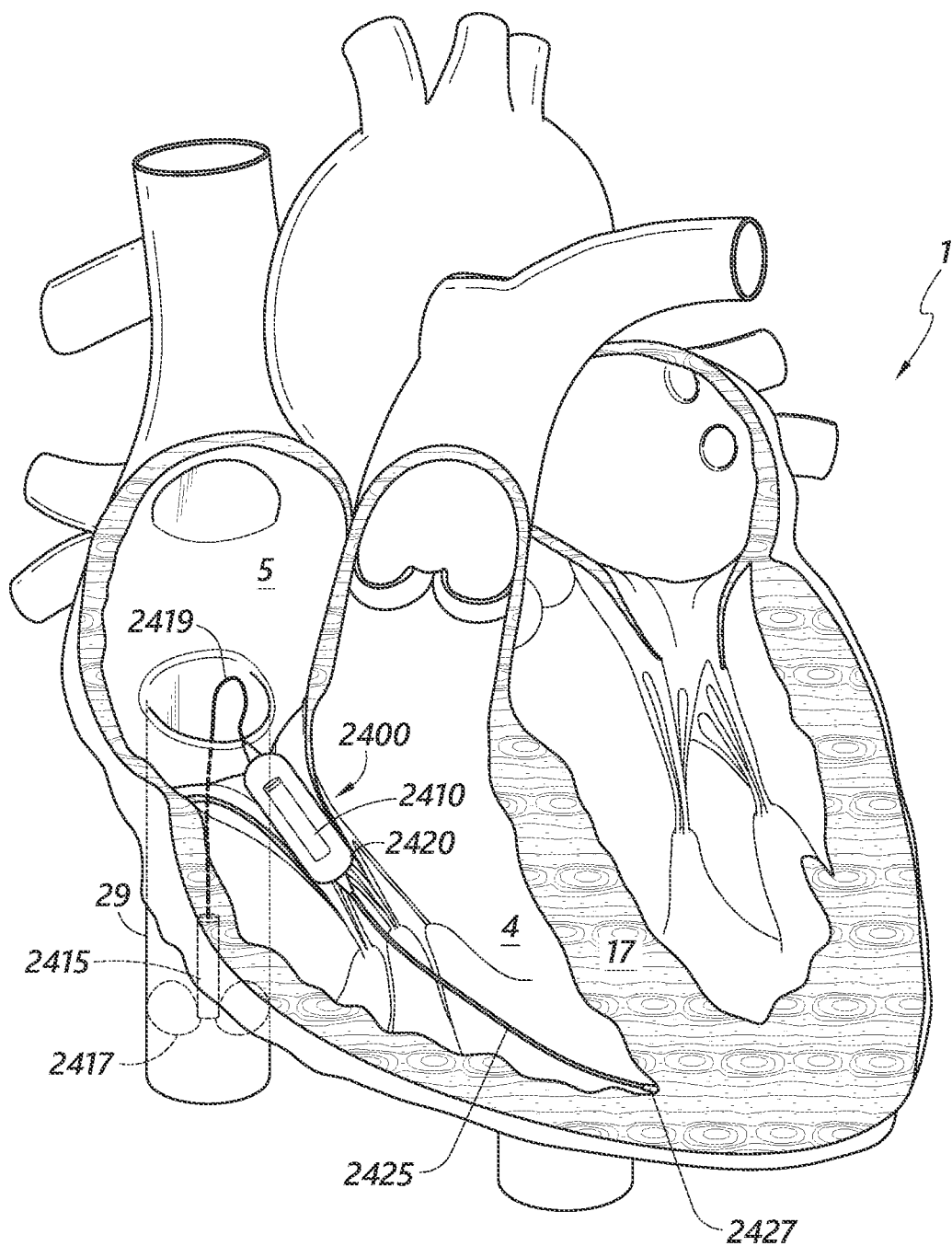
FIG. 24 illustrates a sensor assembly including a sensor-integrated spacer implant device and a tethered separate sensor device in accordance with one or more embodiments.

FIG. 24 illustrates a sensor assembly including a sensor-integrated spacer implant device 2400 and a tethered separate sensor device 2415, which may be anchored in the inferior vena cava or other vessel or anatomy using an anchor 2417. The sensor 2415 may be tethered to the spacer implant device 2400 via a tether 2419, as illustrated. Although the spacer implant device 2400 is shown as being integrated with a sensor 2410, in some embodiments, the spacer 2400 does not include a sensor. The spacer implant device 2400 may be anchored to the ventricular wall by a tether 2425 and/or tissue anchor 2427.

The tethered pressure sensor 2415 anchored in the inferior vena cava 29 may advantageously provide central venous pressure measurements, which may provide a good measure of venous congestion, or other beneficial measurement(s). The anchor 2417 may advantageously be configured to center the pressure sensor 2415 in the vessel 29, which may provide desirable pressure measurement position. Furthermore, the anchor 2417 and/or sensor 2415 may advantageously be configured to, and/or comprise material that serves to, limit tissue overgrowth onto the sensing element of the sensor 2415. The anchor 2417 may further provide an additional anchoring feature for the valve spacer implant 2400, which may further secure the valve spacer implant 2400 in its desired position.

In some embodiments, the pressure sensor 2410 of the valve spacer implant device 2400 may measure right ventricular and/or right atrial pressure, whereas the sensor 2415 may provide measurements of inferior vena cava pressure, which in combination may provide a relatively complete picture of right-sided heart performance. Alternatively, sensors in spacer devices may be implanted in a similar fashion on the left side of the heart.

Figure 25:
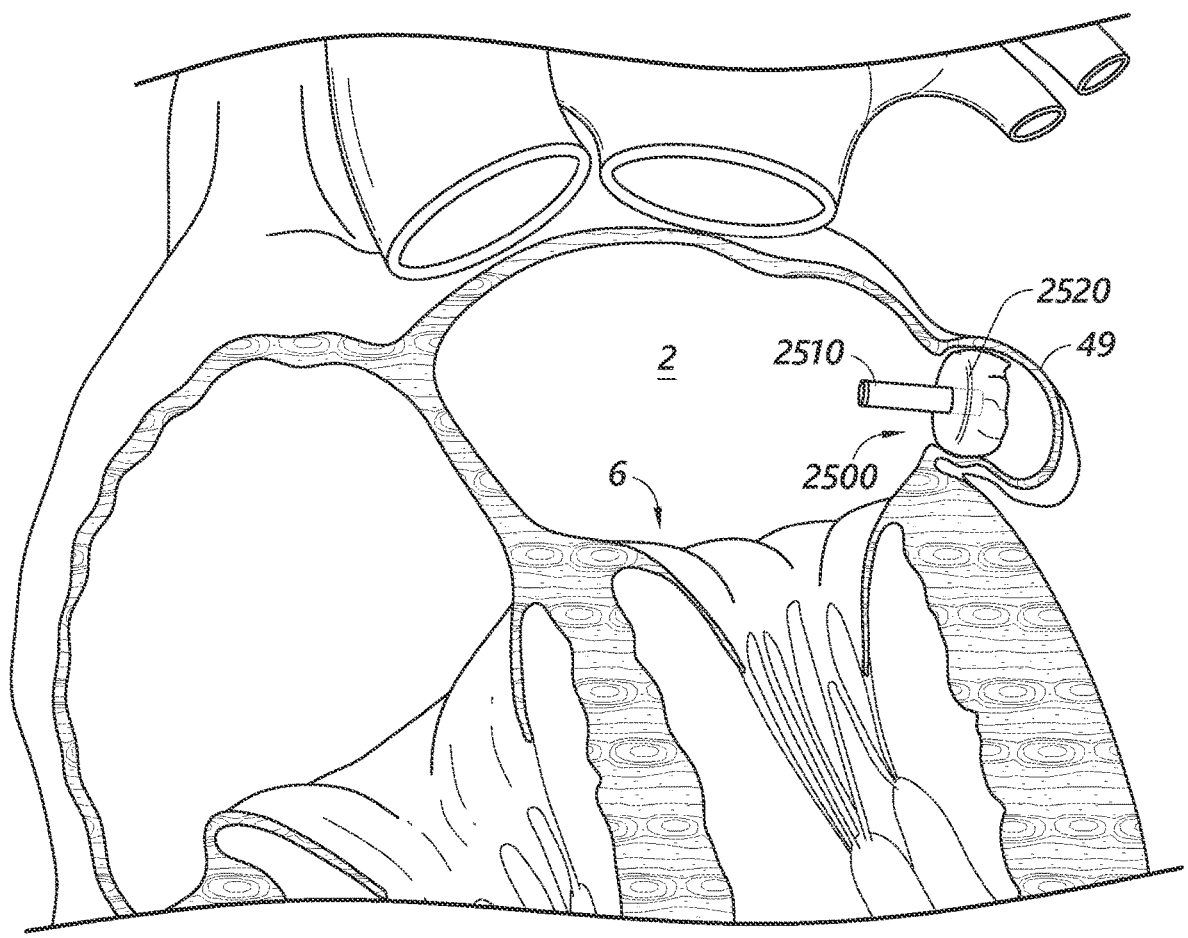
FIG. 25 illustrates a sensor-integrated cardiac implant device comprising a sensor integrated with a left atrial appendage occluder implant device in accordance with one or more embodiments.

In some embodiments, an implant device in accordance with the present disclosure may comprise a sensor integrated with a left atrial appendage implant device. FIG. 25 illustrates a sensor-integrated cardiac implant device 2500 comprising a sensor 2510 integrated with a left atrial appendage occluder implant device 2520. The implant device 2500 may be implanted in a left atrial appendage 49 of a heart. The implant device 2500 can be positioned to measure pressure in the left atrial appendage 49 and/or left atrium 2. Generally, measurement of left atrial pressure may be useful in monitoring fluid build-up the lungs associated with congestive heart failure, as described in detail above. The sensor implant device 2510 may be permanently affixed to the left atrial appendage closure implant device 2520 via or using any attachment or integration mechanism, including bonding, suture wrapping, or other attachment means for fixing the sensor 2510 to the implant 2520. The sensor-integrated implant device 2500 may advantageously provide a secure location for anchoring the atrial pressure monitoring sensor 2510. The sensor 2510 may advantageously be positioned and/or configured to present a relatively low risk of thrombus in the left atrium.

Figure 26:
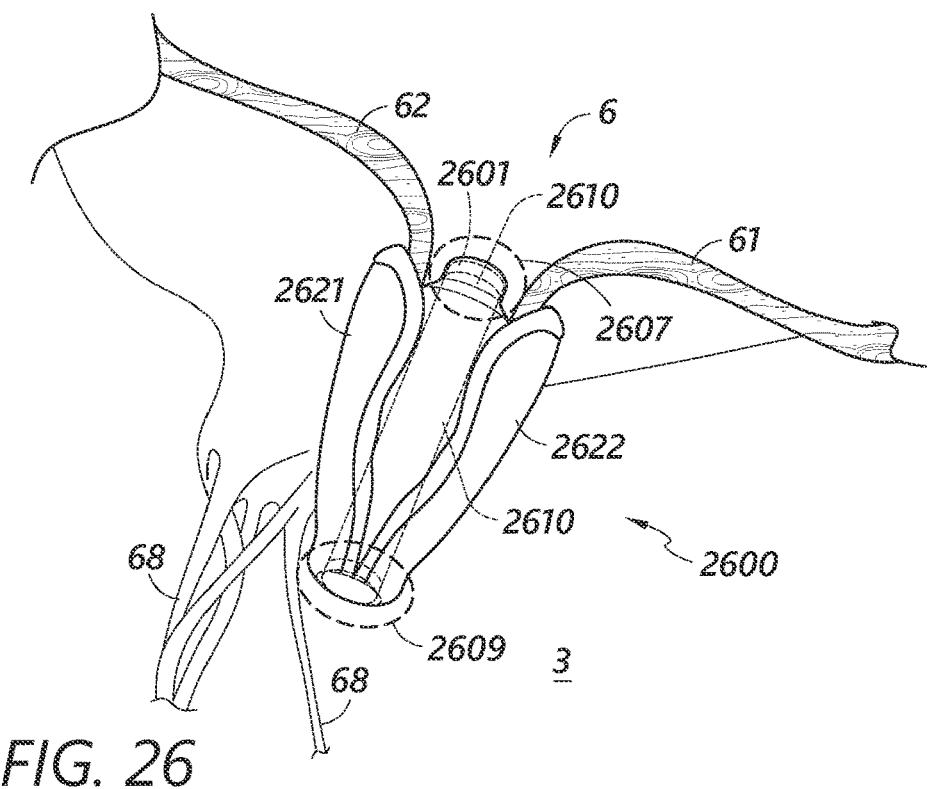
FIGS. 26 and 27 show side and top views, respectively, of a sensor-integrated valve repair implant configured to provide edge-to-edge leaflet attachment for mitral valve repair in accordance with one or more embodiments.
Figure 27:
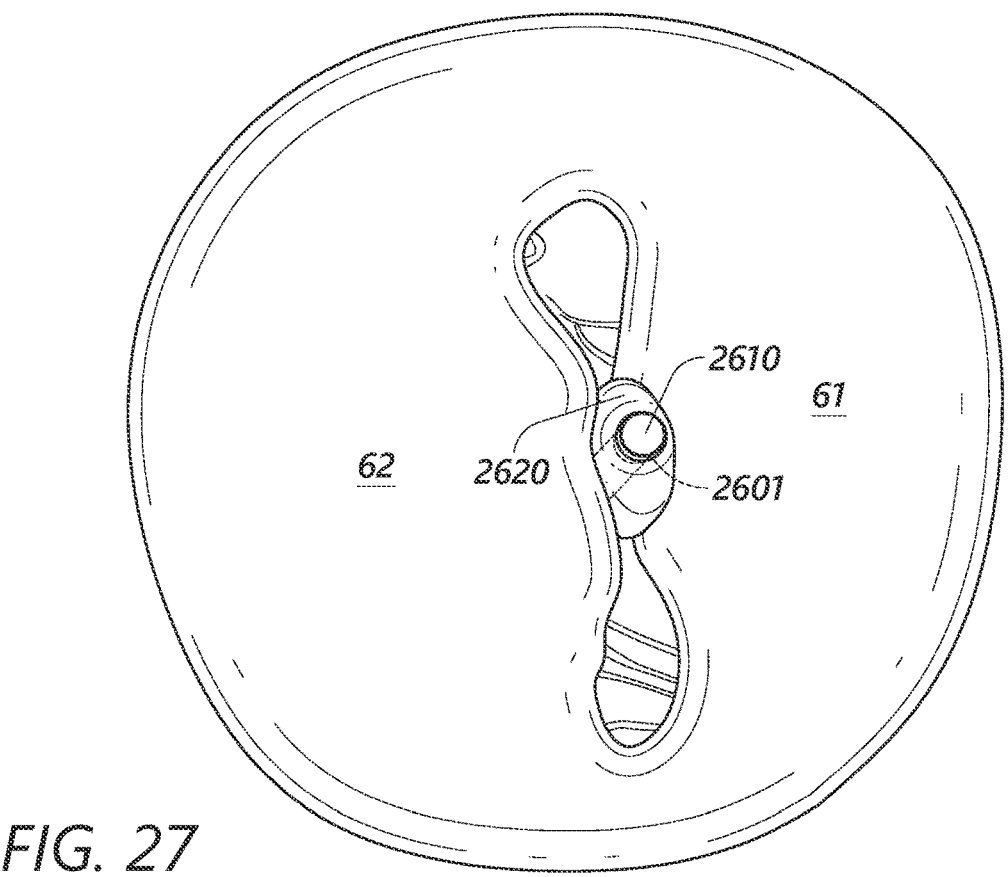

In some embodiments, a sensor-integrated implant device in accordance with the present disclosure comprises a sensor integrated with valve repair clip or device configured to secure the valve leaflets to one another to reduce valve regurgitation. FIGS. 26 and 27 show side and top views, respectively, of a sensor-integrated valve repair implant 2600 configured to provide edge-to-edge leaflet attachment for mitral valve repair in accordance with one or more embodiments of the present disclosure.

Edge-to-edge leaflet repair implemented using the implant device 2600 can advantageously at least partially restore valvular competence by anchoring the free edge of the anterior leaflet 62 of the mitral valve 6 to the corresponding free edge of the posterior leaflet 62, thereby creating a double-orifice valve, as shown in FIG. 27. The implant device 2600 may be deliverable using a transcatheter approach and may therefore be suitable in patients with increased risk for surgical valve-repair solutions.

The implant device 2600 comprises a first clasp member 2621, a second clasp member 2622, and a spacer 2620. The implant 2600 may be configured to capture the valve leaflets between the clasps 2621, 2622 and the spacer 2620, as shows, and may be particularly well for cases of relatively short posterior leaflets or relatively larger leaflet prolapse gaps. The spacer includes a base portion 2609 and an end portion 2607. The base portion 2609 may be considered a ventricle or ventricular portion of the spacer, as the base portion 2609 may be disposed within the ventricle and/or exposed to the ventricle when the implant device 2600 is implanted. The end portion 2607 may be considered an atrium or atrial portion of the spacer, as the end portion 2607 may be disposed within the atrium and/or exposed to the atrium when the implant device 2600 is implanted.

The implant 2600 further comprises a sensor 2610, which may be disposed within and/or integrated with the spacer 2620, as shown. For example, in some embodiments, the sensor 2610 has an exposed sensor element that is positioned and/or configured to generate pressure readings indicative of left atrial pressure. Furthermore, in some embodiments, the implant device 2600 comprises one or more sensor elements positioned and/or configured to provide pressure sensor readings indicating left (or right for tricuspid valve repair) ventricular pressure. For example, such sensor elements may be disposed at or near the base 2609 ventricular portion of the spacer 2620 and/or implant device 2600. In some embodiments, the sensor 2610 is embedded in the spacer 2620.

A sensor element 2601 (e.g., pressure sensor element as described herein) may be exposed and/or protrude from the end portion 2607 of the spacer 2620, such that the sensor element can generate pressure readings associated with the atrial side of the valve 6. In addition to measuring left atrial and/or left ventricular pressure, the sensor 2610 may be used to measure the long-term performance of the repaired valve 6. For example, the sensor 2610 may comprise a dual-element sensor configured to measure the gradient across the valve 6 and/or regurgitation into the left atrium.

Figure 28:
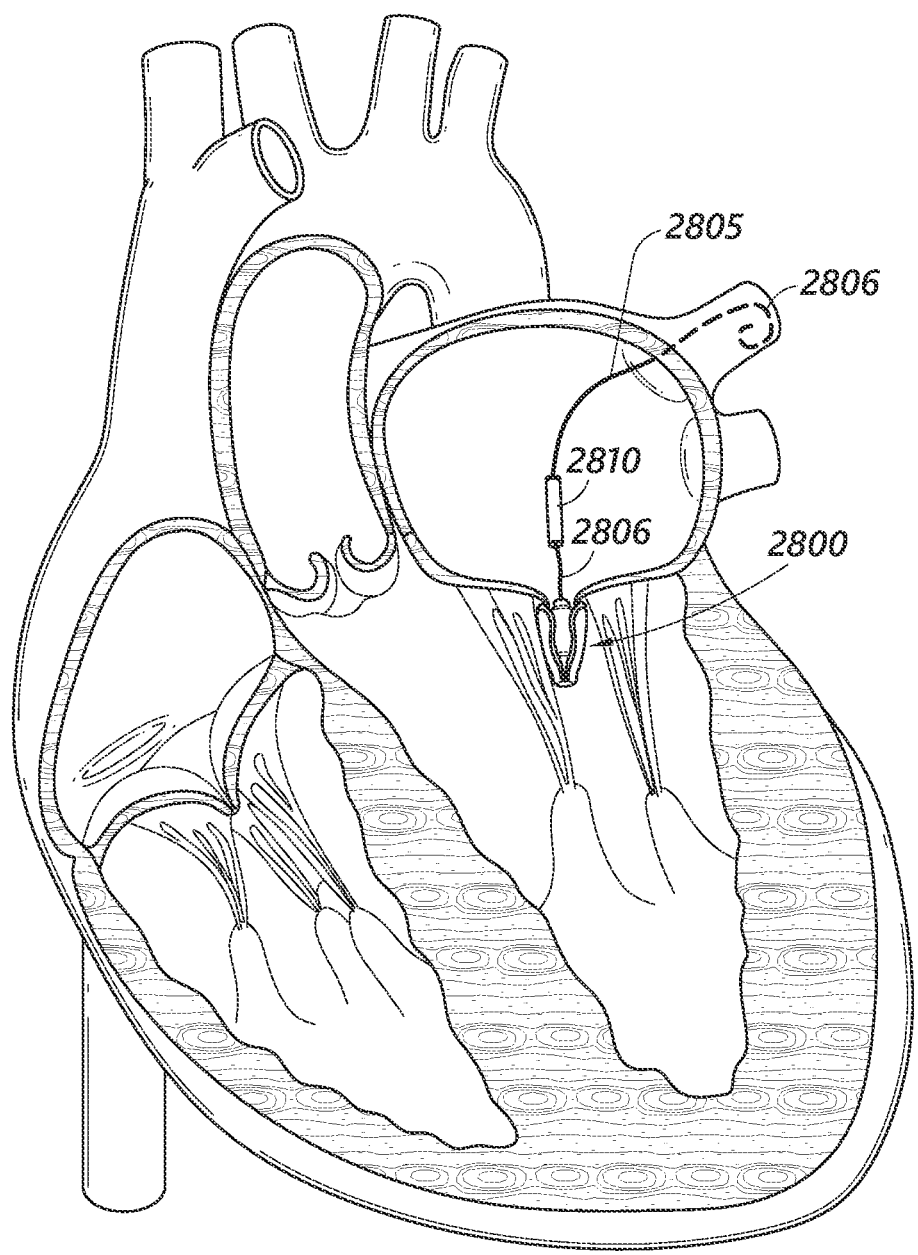
FIG. 28 shows another embodiment of a sensor integrated with a mitral valve repair implant to form a valve repair sensor assembly in accordance with one or more embodiments.

FIG. 28 shows another embodiment of a sensor 2810 integrated with a mitral valve repair implant 2800 to form a valve repair sensor assembly 2801. The assembly 2801 may provide a mechanism for measuring left atrial pressure by tethering a pressure sensor 2810 to the valve repair implant 2800. The assembly 2801 may provide a simplified implant device for integrating pressure sensor functionality with a mitral leaflet repair implant compared to embodiments in which a pressure sensor is integrated with the spacer or other component of the repair clip implant. In some embodiments, the sensor-integrated assembly 2801 further comprises a support strut 2805, which may be coupled or attached to the sensor 2810 in some manner and may serve to further secure the sensor 2810 in a desired position and/or range of positions. In some embodiments, the strut 2805 is at least partially rigid. A distal end 2806 of the strut 2805 may be embedded in tissue to anchor the strut and sensor 2810.

Figure 29:
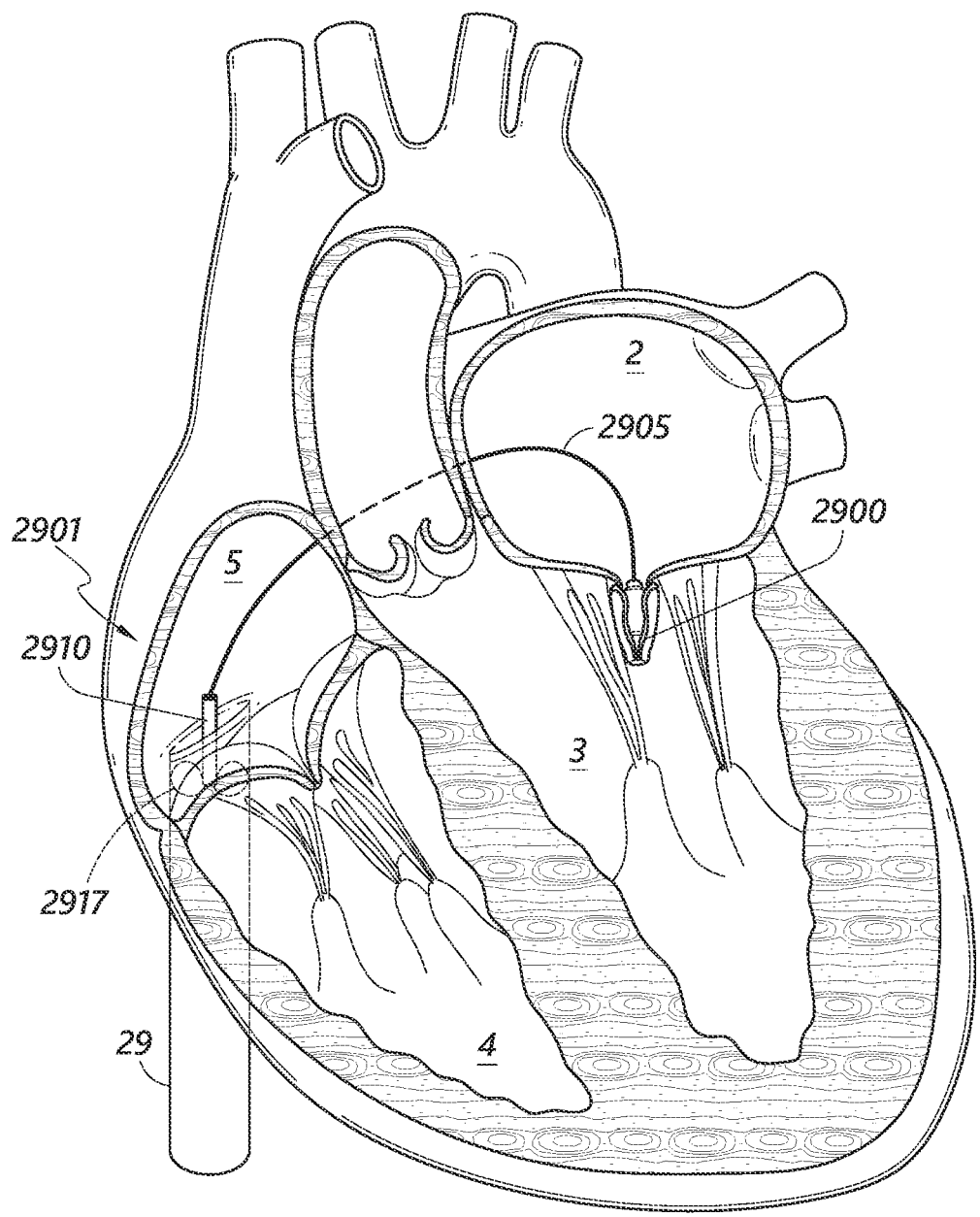
FIG. 29 shows an embodiment of a sensor integrated with a mitral valve repair implant to form a valve repair sensor assembly in accordance with one or more embodiments.

FIG. 29 shows yet another embodiment of a sensor 2910 integrated with a mitral valve repair implant 2900 to form a valve repair sensor assembly 2901. In the embodiment of FIG. 29, the sensor 2910 is anchored in the inferior vena cava 29 by an anchoring feature 2917. The anchor 2917 may be any suitable or desirable anchor in accordance with embodiments of the present disclosure. In some embodiments, the anchor 2917 comprises a memory metal wire frame. The mitral valve repair device 2900 may be implanted using a transseptal access to the left atrium 2. In connection with such procedure, the sensor 2910 may be anchored at least partially within the inferior vena cava or right atrium, wherein a tether 2905 coupling the sensor 2910 to the valve repair device 2900 extends through the interatrial septum wall 18.

Figure 30:
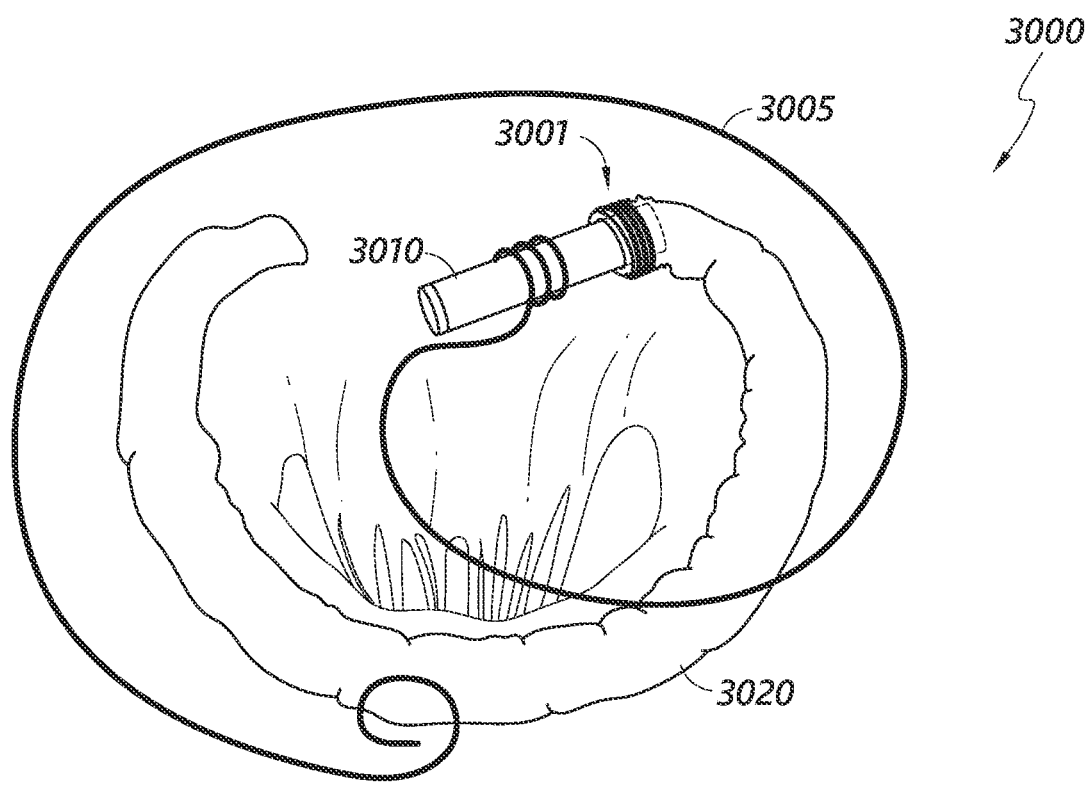
FIG. 30 illustrates a sensor-integrated annular reduction implant in accordance with one or more embodiments.

In some embodiments, sensor-integrated implant devices in accordance with the present disclosure comprise an annular reduction implant device having integrated therewith a sensor, such as a pressure sensor, as described in detail herein. FIG. 30 illustrates a sensor-integrated annular reduction implant 3000 comprising an annular reduction tube 3020 mechanically coupled to a sensor 3010, such as a pressure sensor. In some implementations, the implant device 3000 is configured to be implanted on or adjacent to a native mitral valve annulus.

The annular reduction tube 3020 may comprise a textile tube configured to be sutured or otherwise secured to the native valve annulus and cinched in order to reduce an effective diameter thereof in order to repair the relevant valve. In some embodiments, the sensor-integrated implant device 3000 comprises an anchor wire 3005 that is coupled to the sensor 3010 and configured to further support the sensor 3010 when implanted. For example, the anchor 3005 may comprise a relatively large diameter wire (e.g., memory metal such as Nitinol) that provide support for the sensor 3010. The anchor 3005 may be attached to the sensor 3010 in any way or using any attachment mechanism. For example, as illustrated, the anchor wire 3005 may be wrapped around at least a portion of the sensor 3010. The anchor 35 may be configured to radially expand to provide support within the left atrium or other chamber or blood vessel. In some embodiments, the anchor wire 3005 is configured to be embedded in tissue or is coupled to a tissue anchor element.

In some embodiments, a distal end of the sensor 3005 is secured by the anchor 3005, whereas the proximal end of the sensor 3010 is anchored or secured to a sleeve or other attachment feature of the tube 3020. For example, the tube 3020 may comprise a reducing fitting feature 3001 or other attachment mechanism. The reducing fitting 3001 may be wrapped with suture or other tightening feature for tightening the reducing fitting 3001 around the sensor to thereby secure the sensor 3010 to the tube 3020. Generally, by incorporating the sensor 3010 with an annular reduction implant, the impact on the procedural steps involved with affixing the annular reduction implant to the native valve annulus may be relatively minimal.

Figure 31:
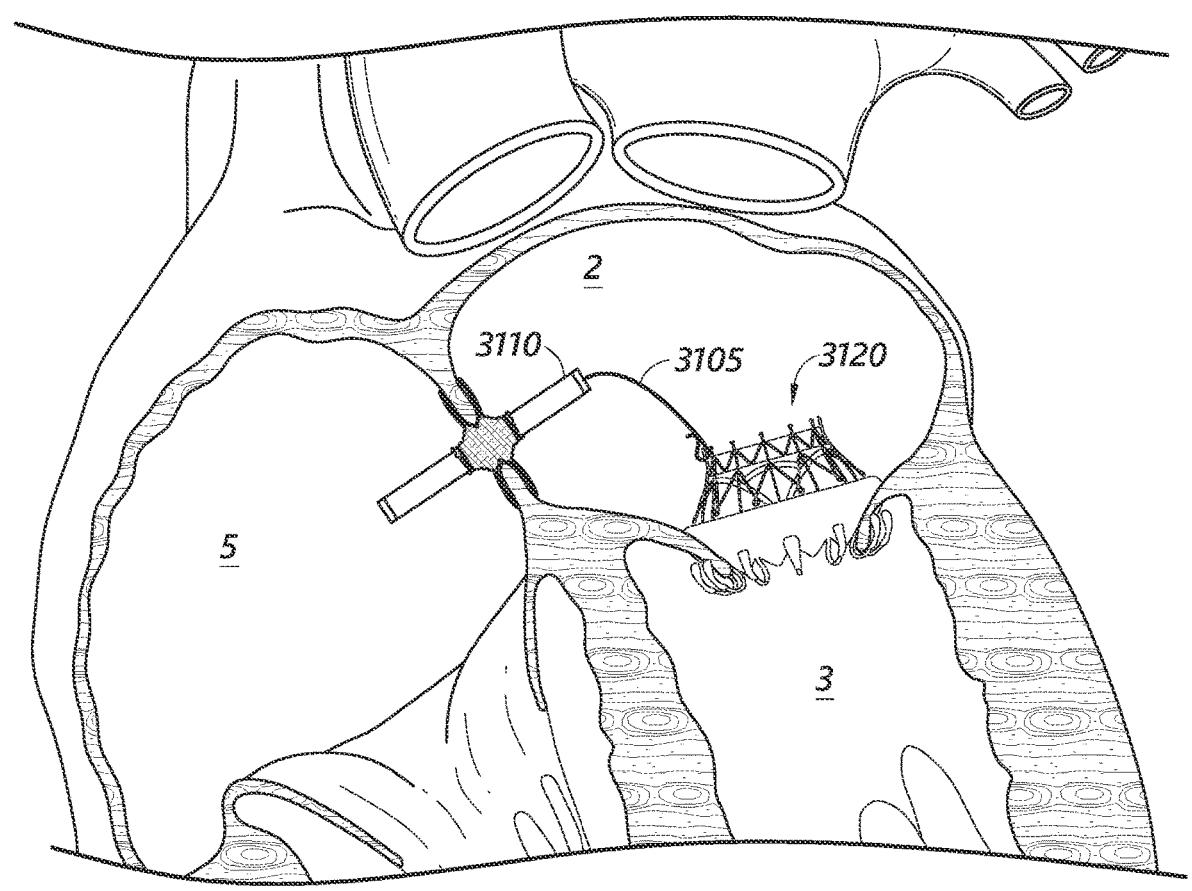
FIG. 31 illustrates a sensor coupled to a replacement mitral valve implant in accordance with one or more embodiments.

FIG. 31 illustrates a sensor 3110 coupled to a replacement mitral valve implant 3120. The combination of the sensor 3110, replacement valve 3120, and coupling structure 3105 may provide a sensor-integrated implant device that may be configured to provide atrial pressure readings as well as valve repair or functionality. In some embodiments, the replacement valve 3120 is a transcatheter heart valve.

Generally, a relatively large delivery system may be required to deliver the transcatheter heart valve 3120 illustrated in FIG. 31. For example, where access to the target implantation site is achieved through the interatrial septum wall 18, such access opening or aperture in the septal wall may be between approximately 6-18 mm in diameter or larger. Therefore, it may be desirable to place a septal closure device in the septal wall to at least partially occlude flow through the septal opening. Described in detail herein are pressure sensor devices integrated with septal closure implants. The illustrated assembly 3101 may advantageously comprise a septal closure structure 3103 with which the sensor device 3110 is integrated, thereby providing septal closure functionality in addition to pressure monitoring and valve repair or functionality. Additionally or alternatively, the coupling structure 3105 may serve as a tether that is incorporated into the frame of the replacement valve 3120, and may be used as an anchor to secure the pressure sensor 3110 in the atrial septum 18 or other position at least partially within the left atrium. Although the valve replacement 3120 is described as a mitral valve replacement, and the atrium 2 is described as the left atrium, it should be understood that the principles disclosed and shown in FIG. 31 apply to other replacement valves, including replacement tricuspid valves, aortic valves, and/or pulmonary valves.

Figure 32:
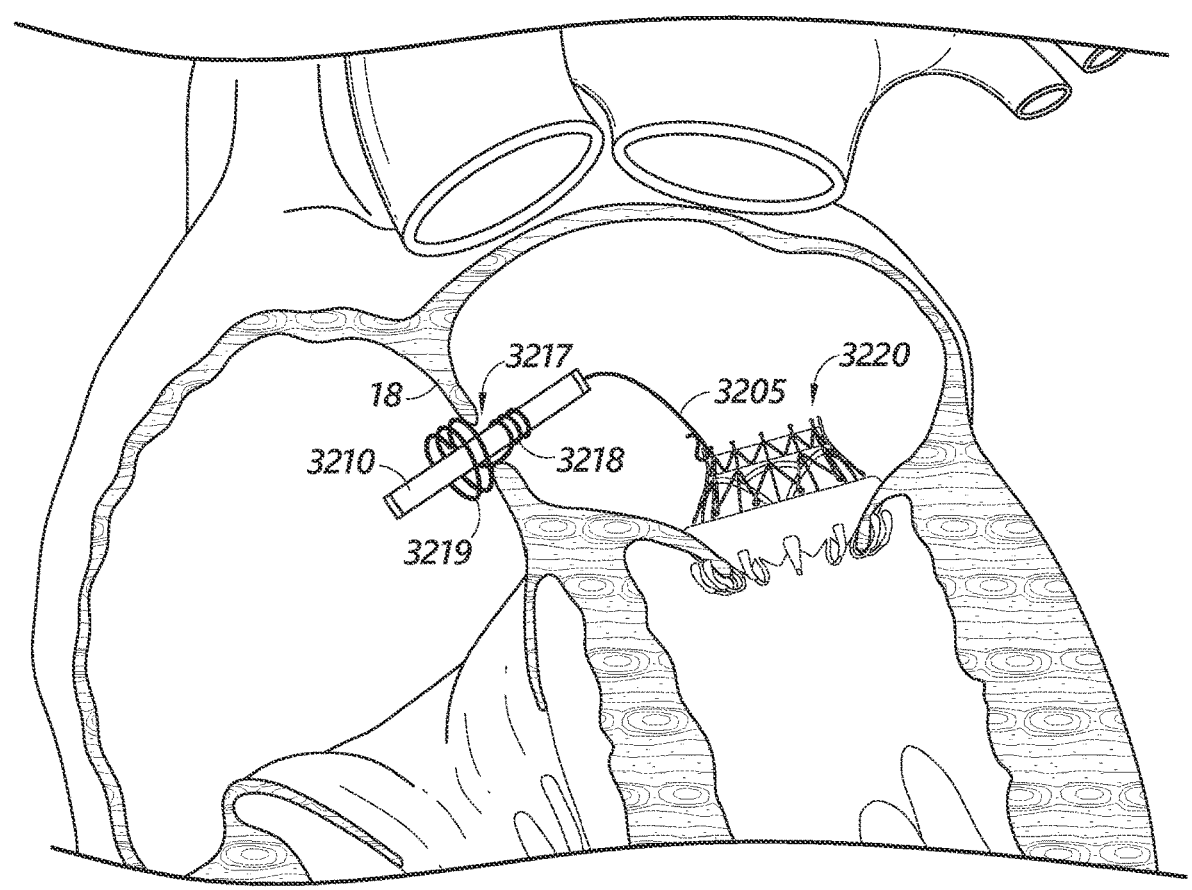
FIG. 32 illustrates a valve repair and pressure sensor assembly in accordance with one or more embodiments.

FIG. 32 illustrates a valve repair and pressure sensor assembly having an alternative anchoring mechanism for the sensor in the tissue wall 18 (e.g. septal wall). In some embodiments, the anchoring of the sensor 3210 may gain one anchoring point from the frame of the replacement valve 3220, as well as another anchoring point from the septal wall, as illustrated. The tissue wall anchor 3217 may comprise a wire shaped into a coil at one end and a hook at another end. For example, the proximal end 3218 of the wire anchor 3217 may be coiled around the sensor 3210 to thereby at least partially secure the sensor 3210. The distal end portion 3219 of the anchor 3217 may be embedded into tissue, and/or may form a larger-diameter coil, as shown, and may have a free end.

The assembly 3201 of FIG. 32 may take advantage of a transseptal access needed to initially place the replacement valve 3220. That is, procedurally, the access, septal crossing, and guide wire may be previously established in connection with placement of the replacement valve 3220, such that introduction of a catheter for transporting the sensor 3210 and associated anchor 3217 may not add substantial complication to the procedure. Furthermore, in some embodiments, the anchor 3217 and sensor 3210 may serve as a septal defect closure device as well.

In some embodiments, a sensor device, such as a pressure sensor device, may be implanted in an atrium or other chamber of the heart and secured at least in part using one or more radially-expanding anchor features or coils. FIG. 33 illustrates a sensor device 3310 suspended in the left atrium 2 of the heart. Although certain embodiments are disclosed herein in the context of the left atrium, it should be understood that sensors in accordance with the present disclosure may be implanted in the right atrium or other chamber or blood vessel of the heart or body. The sensor 3310 is mounted or attached to a relatively large radially-expanding anchor system comprising a radially expanding wire 3305. The wire 3305 may be configured to contact at least a portion of the inner wall of the atrium 2 when expanded. In some embodiments, the wire 3305 is configured to exert outward radial force against the walls of the atrium to thereby secure or even suspend the sensor device 3305 in a central or desired portion of the atrium. Furthermore, the wire 3305 may be at least partially flexible and/or elastic to allow for contracting and/or expanding in response to contraction and expansion of the atrium in connection with cardiac cycles.

The sensor 3310 may be anchored or embedded in the atrial tissue in some embodiments. For example, the sensor 310 may have associated therewith a sensor anchor 3317 configured and dimensioned to be embedded in the tissue of the atrial wall at any suitable or desirable position and/or portion thereof. FIGS. 34A and 34B illustrate example embodiments of pressure sensors having associated or integrated tissue anchors. For example, as shown in FIG. 34A, a pressure sensor 3410 can be associated or integrated with a multiple-prong tissue anchor, as illustrated. Furthermore, as shown in FIG. 34B, a pressure sensor 3411 can be associated or integrated with a corkscrew-type anchor 3418. The anchors of FIGS. 34A and 34B may be incorporated on a distal end of the respective sensors, wherein a shaped wire (e.g. memory metal wire) can be attached to the proximal end of the respective sensor to provide additional stability for the sensor, as illustrated in FIG. 33.

Figure 35:
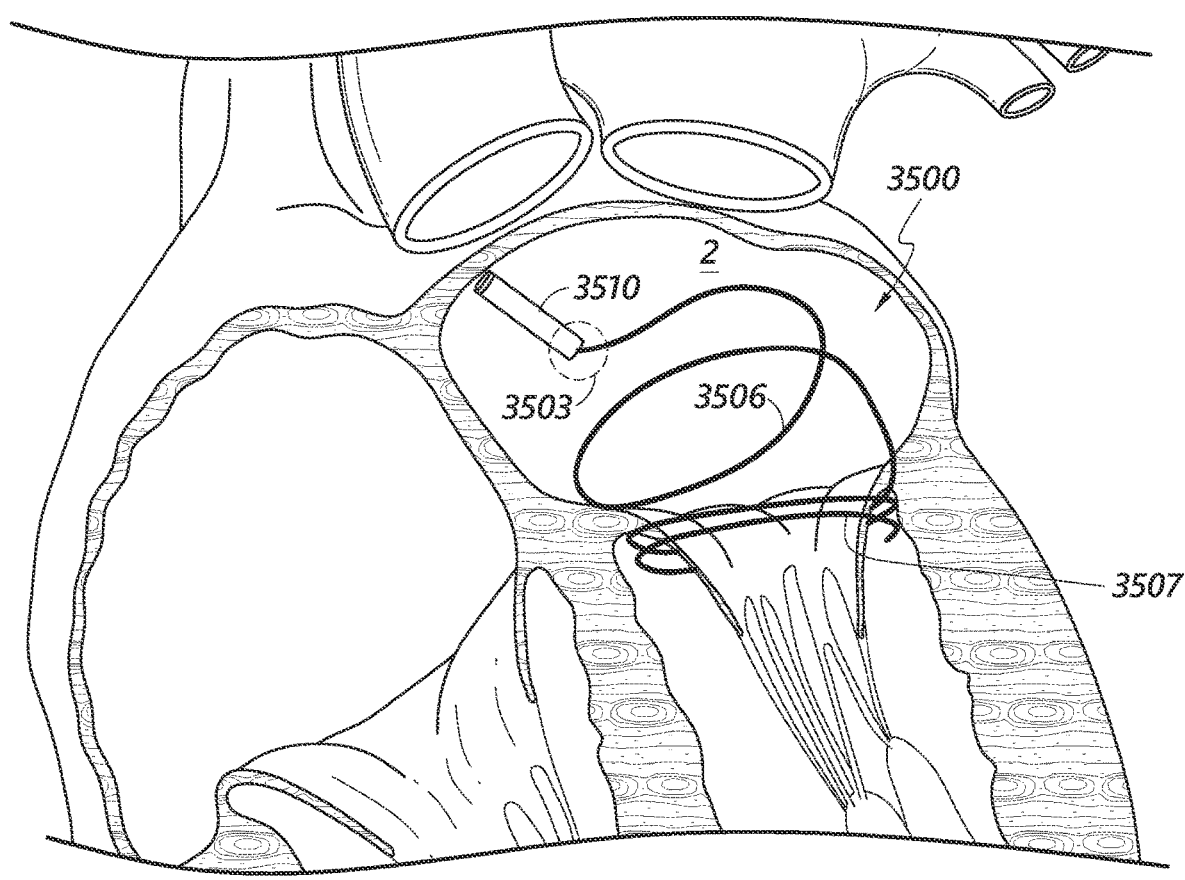
FIG. 35 illustrates a sensor-integrated implant device including a docking device integrated with a sensor in accordance with one or more embodiments.

In some embodiments, a sensor-integrated cardiac implant device in accordance with the present disclosure comprises a pressure sensor integrated with a docking device, such as a docking device for docking a replacement heart valve, or other implant device. Various anchors and docking devices, such as coiled anchors or docking devices, can be used in conjunction with transcatheter heart valves at a native valve annulus (e.g., mitral or tricuspid valve annulus) in order to more securely implant and hold the prosthetic valve at the implantation site. FIG. 35 illustrates a sensor-integrated implant device 3500 including a docking device 3507 integrated with a sensor 3510, such as a pressure sensor.

The anchoring/docking device 3507 can provide a more circular and/or stable annulus at the implantation site, in which prosthetic valves having circular or cylindrically-shaped valve frames or stents can be expanded or otherwise implanted. In addition to providing an anchoring site for a prosthetic valve, the anchoring/docking device 3507 can be sized and shaped to cinch or draw the native valve (e.g., mitral, tricuspid, etc.) anatomy radially inwards. In this manner, one of the main causes of valve regurgitation (e.g., functional mitral regurgitation), specifically enlargement of the heart (e.g., left ventricle) and/or valve annulus, and consequent stretching out of the native valve (e.g., mitral) annulus, can be at least partially offset or counteracted. In some embodiments, the anchoring/docking device 3507 further includes features which, for example, are shaped and/or modified to better hold a position or shape of the docking device during and/or after expansion of a prosthetic valve therein.

The docking device 3507 includes a coil with a plurality of turns extending along a central axis of the docking device. The coil can be continuous and can extend generally helically, with various differently sized and shaped sections. The docking device 3507 shown in FIG. 35 may be configured to best fit at the mitral position, but can be shaped similarly or differently in other embodiments for better accommodation at other native valve positions as well.

The pressure sensor 3510 can be integrated with or attached to the proximal end 3503 of the docking device 3507. In implanting the docking/sensor assembly 3500, the sensor 3510 may be advanced to engage with the docking device 3507. Additional anchoring features (not shown) may be added to secure the proximal end of the sensor 3510 to the septal wall or other wall of the atrium 2. In some embodiments, the sensor 3510 is anchored to the septal wall and integrated with a septal closure device as described herein. In some embodiments, the docking device 3507 includes one or more proximal coils or loops 3506, which may be configured to assume a shape that can contact one or more portions of the inner wall of the atrium 2 to thereby at least partially secure the sensor 3510 in a desired position. Although a single proximal coil/loop 3506 is shown, the docking device 3507 may have any suitable or desirable number of coils/loops, or other shape and/or configuration features for securing or stabilizing the sensor 3510.

Figure 36A:
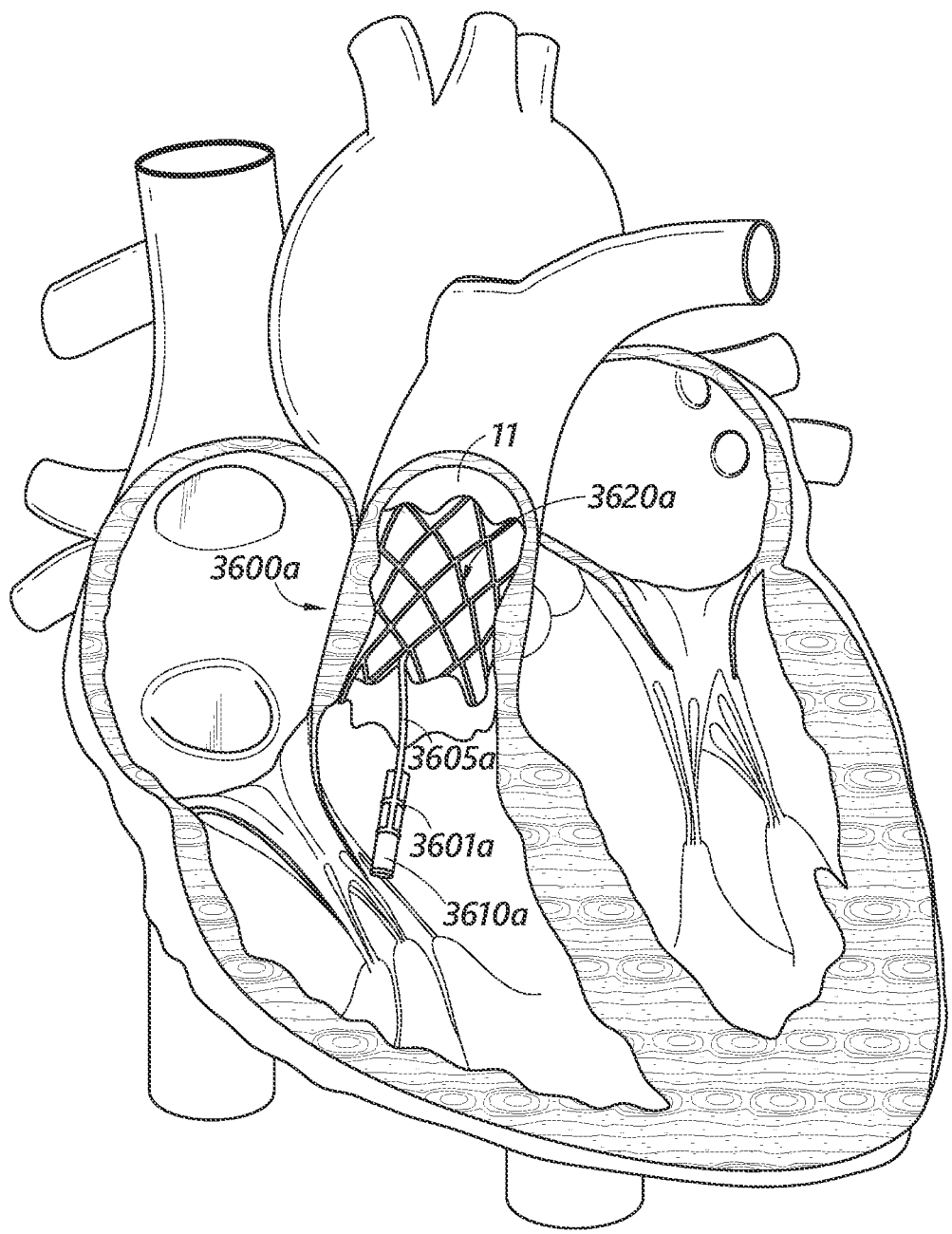
FIGS. 36A and 36B illustrate sensor-integrated cardiac implant devices in accordance with one or more embodiments.
Figure 36B:
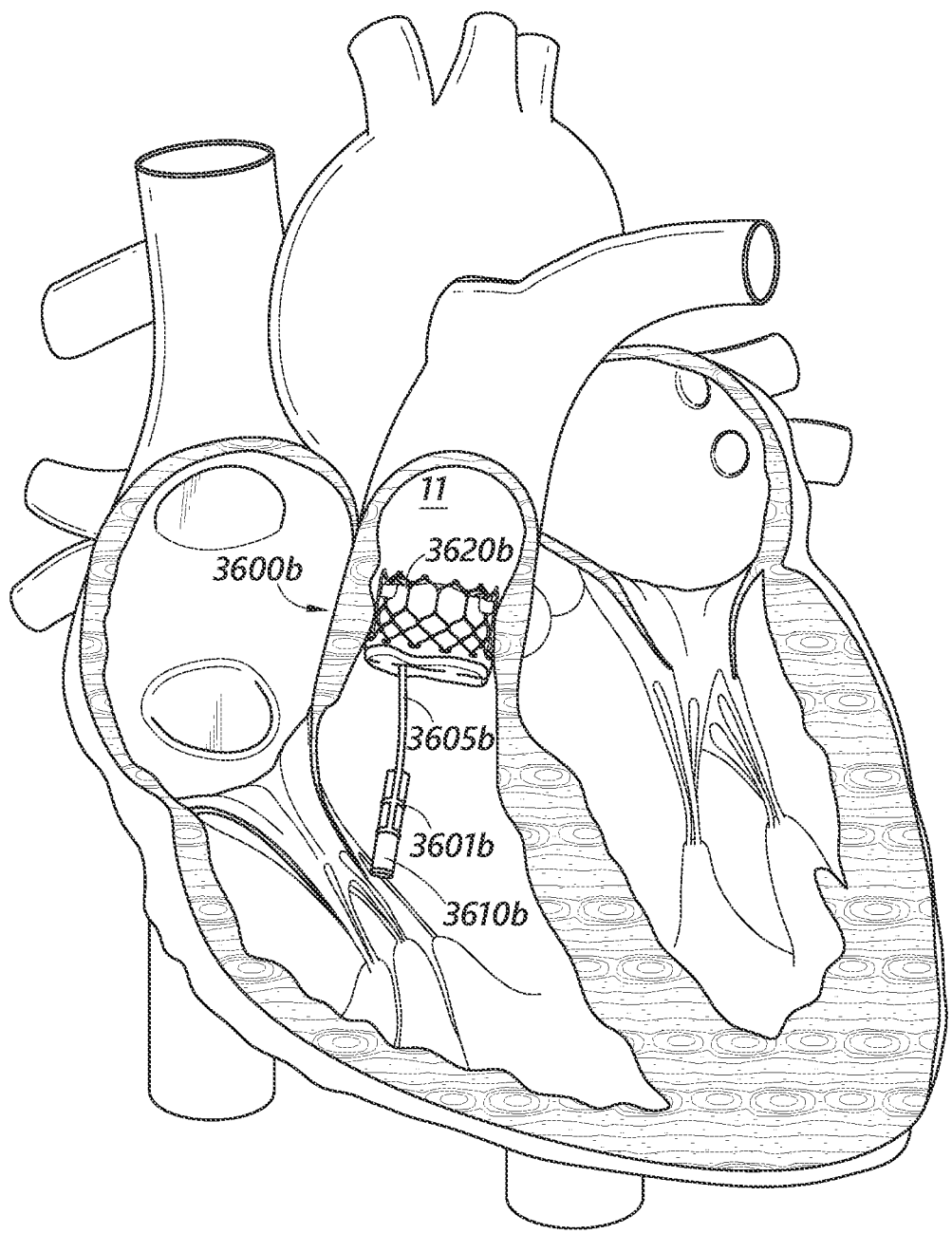

FIGS. 36A and 36B illustrate sensor-integrated cardiac implant devices 3600a, 3600b in accordance with one or more embodiments of the present disclosure. The cardiac implant devices 3600a, 3600b include cardiac implant structures 3620a, 3620b, which are implanted and/or secured within the pulmonary artery 11. The cardiac implant structures may comprise a pulmonary valve replacement device 3620b and/or pulmonary stent device 3620a. For example, percutaneous pulmonary valve replacement 3620b can be an effective means by which to restore valve function for defective pulmonary valves. In some cases, the pulmonary artery may be at least partially dilated, and thus a reducer stent 3620a may desirably be placed in the pulmonary artery prior to percutaneous placement of a replacement valve. Therefore, the cardiac implant structure 3620a may comprise a reducer stent, which may include struts configured and designed to anchor and position the pressure sensor 3610a such that the sensing element of the pressure sensor 3610a is positioned at or near the center of the pulmonary artery 11. To such end, the cardiac implant structures 3620a, 3620b may comprise an arm or strut 3605a, 3605b, which may have one or more attachment features 3601a, 3601b for attaching the sensor 3610a, 3610b thereto, such as one or more bands, straps, features, locking features, and/or other attachment means. In some embodiments, the strut or arm feature 3605 comprises memory metal shaped to receive and/or anchor the sensor 3610. The stent structure 3620 may be sized to have placed therein a valve replacement device. Furthermore, although a stent is shown in FIG. 36, it should be understood that in some embodiments the cardiac implant structure 3620 comprises a replacement pulmonary valve device.

Figure 37:
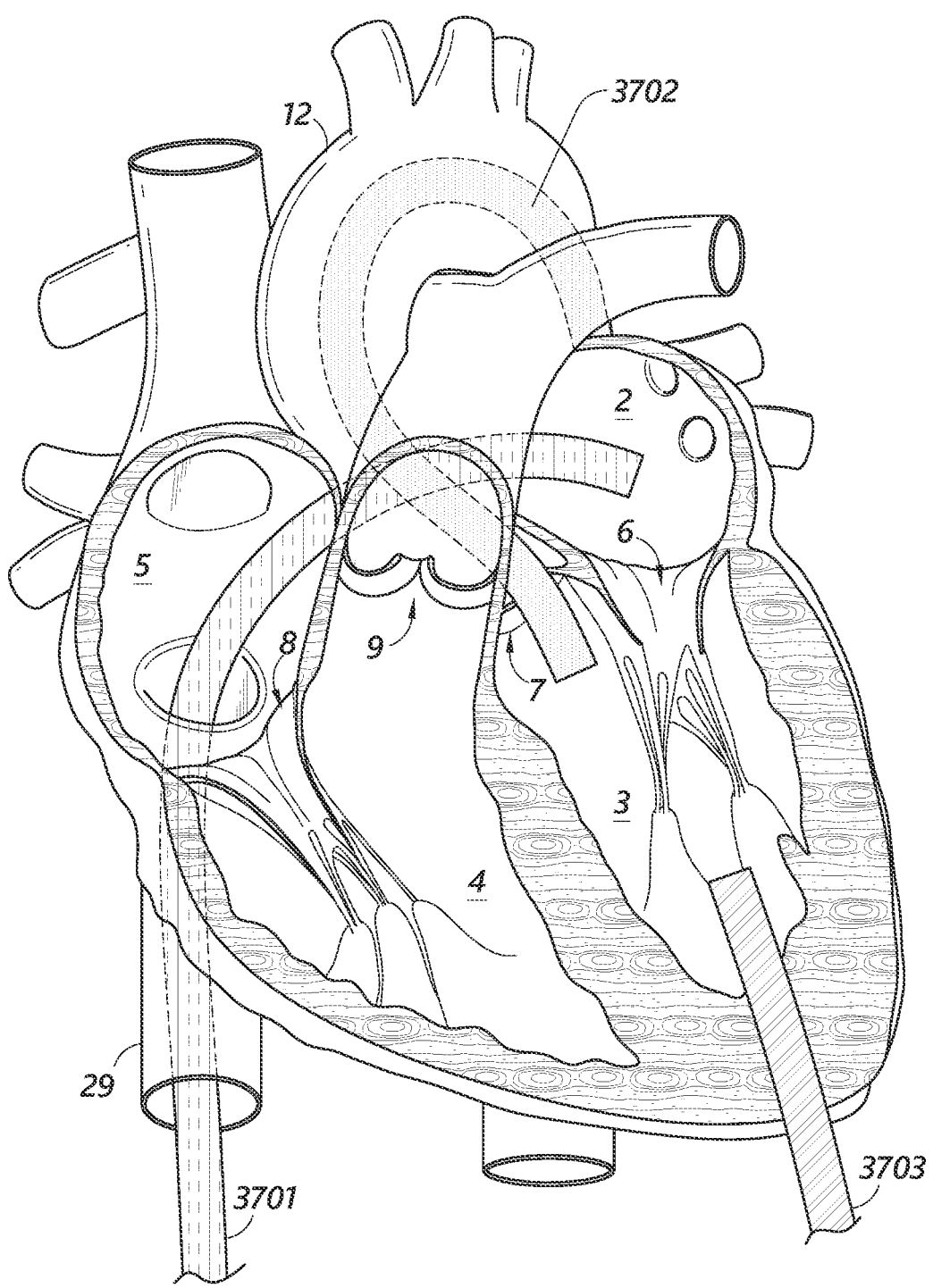
FIG. 37 illustrates various access paths through which access to a target cardiac anatomy may be achieved in accordance with one or more embodiments.

The various embodiments disclosed herein relate to sensor-integrated cardiac implant devices, which may be implanted in any heart chamber or blood vessel. With respect to embodiments relating to implant devices implanted in one or more of the left or right atria and/or one or more of the left right ventricles, or in one or more blood vessels accessed through one or more atria or ventricles, such access may be achieved in any suitable or desirable way. For example, FIG. 37 illustrates various access paths through which access to a target cardiac anatomy may be achieved, including transseptal access 3701, which may be made through the inferior vena cava 29 or superior vena cava 19, and from the right atrium 5, through the septal wall (not shown) and into the left atrium 2. For transaortic access 3702, a delivery catheter may be passed through the descending aorta, aortic arch 12, ascending aorta, and aortic valve 7. For transapical access 3703, access may be made directly through the apex of the heart and into the left ventricle 3 or right ventricle 4.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A septal closure device comprising:
   a wireform frame comprising:
      a central portion defining a circular shape; and
      a plurality of anchor loops that project radially outward from the central portion, each of the plurality of anchor loops forming a respective internal void;
   a planar occluding membrane formed as a sheet coupled to the central portion of the wireform frame and spanning a central void within the central portion of the wireform frame, the central void and occluding membrane lying in a plane that is perpendicular to an ax is of the circular shape of the central portion; and
   a pressure sensor device attached to the occluding membrane;
   wherein:
      the occluding membrane sheet covers an entirety of the central void within the central portion outside of a portion occupied by the pressure sensor device;
      the occluding membrane sheet does not cover the internal voids of the plurality of anchor loops;
      the pressure sensor device comprises a first portion disposed on a first side of the occluding membrane sheet and a second portion disposed on a second side of the occluding membrane sheet; and
      the pressure sensor device is supported solely by the occluding membrane sheet and not directly by the wireform frame.

2. The septal closure device of claim 1, wherein the first portion of the pressure sensor device comprises a first pressure sensor element, and the second portion of the pressure sensor device comprises a second pressure sensor element.

3. The septal closure device of claim 1, wherein the occluding membrane comprises a cloth, the cloth holding the pressure sensor device in suspension.

4. The septal closure device of claim 1, wherein the occluding membrane comprises woven polymer fibers.

5. The septal closure device of claim 1, wherein the pressure sensor device comprises a rigid cylindrical body.

6. The septal closure device of claim 1, wherein, in a non-deflected configuration, the plurality of anchor loops are coplanar with the central portion.

7. The septal closure device of claim 1, wherein each of the plurality of anchor loops has a radially inner neck that is open to the central void of the wireform frame.

8. The septal closure device of claim 1, wherein:
the plurality of anchor loops comprises four angularly distributed diamond-shaped loop anchors emanating from the central portion of the wireform frame;
the central portion of the wireform frame has a form of a segmented ring lying in the plane perpendicular to the axis of the central portion; and
the pressure sensor device passes through the occluding membrane, the pressure sensor device being co-axial with the axis of the central portion of the wireform frame.

9. The septal closure device of claim 8, wherein each of the four angularly distributed loop anchors originates at a neck portion defined by and emanating from end portions of adjacent segments of the segmented ring and expands moving radially outward to form the diamond shape.

10. The septal closure device of claim 8, wherein:
a first loop anchor and a second loop anchor of the four angularly distributed loop anchors each include an eyelet at a distal end of the respective loop anchor; and
the first loop anchor and the second loop anchor are positioned opposite one another about the segmented ring.

11. The septal closure device of claim 1, wherein
the wireform frame comprises a plurality of arc segments that define the circular shape of the central portion, the central portion having a form of a circular boundary with a plurality of angular breaks;
the occluding membrane sheet comprises a cloth having a perimeter attached to the central portion.

12. The septal closure device of claim 11, wherein the plurality of anchor loops have neck regions defining the plurality of angular breaks of the circular boundary.

13. The septal closure device of claim 1, wherein the wireform frame is formed from a single, continuous wire.

14. The septal closure device of claim 1, wherein each of the plurality of anchor loops has a diamond shape with a width that is greater than a length of the anchor loop.

* * * * *